US009393326B2

(12) United States Patent
Jaffray et al.

(10) Patent No.: US 9,393,326 B2
(45) Date of Patent: *Jul. 19, 2016

(54) COMPOSITIONS AND METHODS FOR MULTIMODAL IMAGING

(71) Applicant: University Health Network, Toronto, Ontario (CA)

(72) Inventors: David Jaffray, Etobicoke (CA); Christine Allen, Toronto (CA); Jinzi Zheng, Toronto (CA); Raymond Matthew Reilly, Brampton (CA); Gregory Jason Perkins, Kingston (JM)

(73) Assignee: University Health Network, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/205,670

(22) Filed: Mar. 12, 2014

(65) Prior Publication Data
US 2014/0193330 A1 Jul. 10, 2014

Related U.S. Application Data

(63) Continuation of application No. 11/816,054, filed as application No. PCT/CA2006/000207 on Feb. 10, 2006, now Pat. No. 8,703,097.

(60) Provisional application No. 60/651,638, filed on Feb. 11, 2005.

(51) Int. Cl.
| | |
|---|---|
| *A61K 49/00* | (2006.01) |
| *A61K 51/00* | (2006.01) |
| *A61K 49/04* | (2006.01) |
| *A61B 5/00* | (2006.01) |
| *A61B 6/00* | (2006.01) |
| *A61B 8/08* | (2006.01) |
| *A61K 9/127* | (2006.01) |
| *A61K 49/18* | (2006.01) |
| *A61K 51/12* | (2006.01) |
| *A61B 5/055* | (2006.01) |
| *A61B 8/00* | (2006.01) |

(52) U.S. Cl.
CPC ............... *A61K 49/04* (2013.01); *A61B 5/415* (2013.01); *A61B 5/418* (2013.01); *A61B 6/00* (2013.01); *A61B 6/5247* (2013.01); *A61B 8/5238* (2013.01); *A61K 9/127* (2013.01); *A61K 9/1271* (2013.01); *A61K 49/0002* (2013.01); *A61K 49/0466* (2013.01); *A61K 49/1812* (2013.01); *A61K 51/1234* (2013.01); *A61B 5/055* (2013.01); *A61B 8/00* (2013.01)

(58) Field of Classification Search
CPC ........ A61K 49/00; A61K 49/18; A61K 51/00
See application file for complete search history.

(56) References Cited

U.S. PATENT DOCUMENTS

| | | | | |
|---|---|---|---|---|
| 5,242,683 | A | * | 9/1993 | Klaveness ..................... 424/9.35 |
| 5,312,617 | A | * | 5/1994 | Unger et al. ................. 424/9.365 |
| 5,482,699 | A | * | 1/1996 | Almen et al. ................. 424/9.42 |
| 5,676,928 | A | | 10/1997 | Klaveness et al. |
| 2005/0084453 | A1 | | 4/2005 | Ueda et al. |
| 2005/0129750 | A1 | * | 6/2005 | Hu et al. ........................ 424/450 |
| 2006/0182687 | A1 | | 8/2006 | Yang et al. |

FOREIGN PATENT DOCUMENTS

CA 2459724 A1 3/2003

OTHER PUBLICATIONS

Mulder et al., "MR molecular imaging and fluorescence microscopy or identification of activated tumor endothelium using a bimodal lipidic nanoparticle", The FASEB Journal, vol. 19, Dec. 2005, pp. 2008-2010.
Rubin et al., "Formulation of Radiographycally Detectable Gastrointestinal Contrast Agents for Magnetic Resonance Imaging: Effects of Barium Sulfate Additive on MR Contrast Agent Effectiveness", Magn. Reson. Med., 1992, vol. 23, pp. 154-165.I. 280, No. 3, pp. 1319-1327.
Lanza et al., "Targeted Antiproliferative Drug Delivery to Vascular Smooth Muscle Cells with a Magnetic Resonance Imaging Nanoparticle . . . ", Circulation, Nov. 2002, vol. 106, No. 22, pp. 2842-2847.
Lanza et al., "Molecular imaging in MR with targeted paramagnetic nanoparticles", Medicamundi, Apr. 2003, vol. 47, No. 1, pp. 34-39.
Hughes et al., "Targeted ultrasonic contrast agents for molecular imaging and therapy: a brief review", Medicamundi, Apr. 2003, vol. 47, No. 1, pp. 66-73.
Winter et al., "Molecular Imaging of Angiogenesis in Early-Stage Artherosclerosis with αvβ3-Integrin-Targeted Nanoparticles", Circulation, Nov. 2003, vol. 88, No. 5, pp. 2270-2274.
Fossheim et al., Paramagnetic Liposomes as Magnetic Resonance Imaging Contrast Agents, Invest Radiol, vol. 33 (11), 810-821, 1998.
Parr et al., "Accumulation of Liposomal Lipid and Encapsulated Doxorubicin in Murine Lewis Lung Carcinoma: The Lack of Beneficial Effects by Coating Liposomes with Poly(ethylene glycol)", J. Pharmacol. Exper. Ther., 1997, vol. 280, No. 3, pp. 1319-1327.
Perkins et al. "Nanoengineered multimodal contrast agent for medical imaging guidance", Medical Imaging 2005: Physiology, Function and Structure from Medical Images, Proceedings of SPIE, 2005, vol. 5746, pp. 31-39.

\* cited by examiner

*Primary Examiner* — Michael G Hartley
*Assistant Examiner* — Jagadishwar Samala
(74) *Attorney, Agent, or Firm* — Rothwell, Figg, Ernst & Manbeck, P.C.

(57) ABSTRACT

There is provided signal modifying compositions for medical imaging comprising a carrier and signal modifying agents specific for two or more imaging modalities. The compositions are characterized by retention efficiency, with respect of the signal modifying agents that enables prolonged contrast imaging without significant depletion of the signal modifying agent from the carrier. The carriers of the present invention are lipid based or polymer based the physico-chemical properties of which can be modified to entrap or chelate different signal modifying agents and mixtures thereof and to target specific organs or tumors or tissues within a mammal.

37 Claims, 20 Drawing Sheets

COMPOSITIONS AND METHODS FOR MULTIMODAL IMAGING

This application is a continuation of Ser. No. 11/816,054 filed Dec. 6, 2007, which is a 35 U.S.C. 371 National Phase Entry Application from PCT/CA06/00207, filed Feb. 10, 2006, which claims the benefit of U.S. Provisional Application No. 60/651,638 filed on Feb. 11, 2005, the disclosures of which are incorporated herein in their entirety by reference.

FIELD OF THE INVENTION

This invention relates to the field of medical imaging and more specifically to the use of signal modifying agents in medical imaging.

BACKGROUND OF THE INVENTION

In recent years significant effort has been devoted to the development of multimodality imaging. Since each medical imaging modality has unique strengths and limitations, it is often through the compound use of multiple modalities that the complete assessment of a patient is achieved. Interest in the area of multimodality imaging has also been prompted by the realization that such techniques offer much more sophisticated characterization of the morphology and physiology of tissues and organs, and that confidence gained in the accurate correspondence or registration of different modalities greatly enhances their value (Barillot C, Lemoine D, Le Briquer L, et al. *Eur J Radiol* 1993; 17:22-27.). Consequently, this improved value of imaging will ultimately allow for advances in diagnosis and evaluation of disease, image-guided therapeutic interventions, and assessment of treatment outcomes. The recent integration of computed tomography (CT) and positron-emission tomography (PET) systems is a good example of the advantages of the multimodal approach (Townsend D W. *Mol Imaging Biol* 2004; 6:275-290; Townsend D W, Carney J P, Yap J T, et al. *J Nucl Med* 2004; 45 Suppl 1:4S-14S; Townsend D W, Beyer T. *Br J Radiol* 2002; 75 Spec No:S24-30). The CT-PET combination has revolutionized the utilization of PET and served to increase the specificity of PET-based assessment. In the context of radiation therapy, there is a need to merge CT and magnetic resonance (MR) imaging with CT employed for 3D volumetric dose calculation (Rosenman J G, Miller E P, Tracton G, et al. *Int J Radiat Oncol Biol Phys* 1998; 40:197-205.) and MR for accurate delineation of the target and normal structures as it provides exceptional soft tissue definition. For example, accurate delineation and targeting of the prostate gland in radiation therapy of prostate cancer necessitates parallel use of CT and MR imaging (Rasch C, Barillot I, Remeijer P, et al. *Int J Radiat Oncol Biol Phys* 1999; 43:57-66.). Furthermore, CT technology in the form of conventional and cone-beam systems is employed on a daily basis to guide the delivery of radiation therapy on treatment machines (Uematsu M, Sonderegger M, Shioda A, et al. *Radiother Oncol* 1999; 50: 337-339; Jaffray D A, Siewerdsen J H, Wong J W, et al. *Int J Radiat Oncol Biol Phys* 2002; 53:1337-1349.).

Clinical imaging in all modalities requires an adequate level of differential contrast relative to noise be achieved in order to identify the structures or phenomena under observation. Although imaging on CT and MR can be performed without the administration of signal modifying agents there are numerous instances in both disease diagnosis and treatment, in which procedures benefit from the improved contrast and dynamics that are added by the use of these agents (Krause W. *Adv Drug Deliv Rev* 1999; 37: 159-173; Saeed M, Wendland M F, Higgins C B. *J Magn Reson Imaging* 2000; 12:890-898).

To date, although a multitude of signal modifying agents are commercially available for single modality imaging, few attempts have been made to develop signal modifying agents that can be used across multiple imaging modalities (McDonald M A, Watkin B S, Watkin K L. Small *Invest Radiol* 2003; 38:305-310; Bloem J L, Wondergem J. *Radiology* 1989; 171:578-579; Gierda D S, Bae K T. *Radiology* 1999; 210: 829-834; Quinn A D, O'Hare N J, Wallis F J, et al. *J Comput Assist Tomogr* 1994; 18: 634-636; Pena C S, Kaufman J A, Geller S C, et al. *J Comput Assist Tomogr* 1999; 23:23-24.). The lack of development in this area is likely due to challenges presented by the fact that the distinct imaging modalities have different sensitivities for different signal modifying agents (Krause W. *Adv Drug Deliv Rev* 1999; 37: 159-173.). A simple approach for realizing a multimodal signal modifying agent for CT and MR has been to exploit commercially available extracellular gadolinium-based signal modifying agents for enhancement in both of these modalities. In this case, the properties of gadolinium that allow for use in both CT and MR include its relatively high atomic number and paramagnetic characteristics (McDonald M A, Watkin B S, Watkin K L. Small *Invest Radiol* 2003; 38: 305-310; Bloem J L, Wondergem J. *Radiology* 1989; 171: 578-579; Gierda D S, Bae K T. *Radiology* 1999; 210: 829-834; Quinn A D, O'Hare N J, Wallis F J, et al. *J Comput Assist Tomogr* 1994; 18:634-636; Pena C S, Kaufman J A, Geller S C, et al. *J Comput Assist Tomogr* 1999; 23:23-24.). However, due to their low molecular weight, these agents only remain in the vascular system for a short period of time, exhibit rapid dynamic distribution changes in different organs and are excreted quickly. The use of these agents for cross-modality imaging would therefore require both multiple administrations and fast imaging sequences. Also, the low gadolinium payload per molecule, relative to conventional iodinated signal modifying agents, would necessitate the administration of higher doses for adequate CT enhancement which may have implications in terms of both cost and toxicity (McDonald M A, Watkin B S, Watkin K L. Small *Invest Radiol* 2003; 38:305-310; Bloem J L, Wondergem J. *Radiology* 1989; 171: 578-579; Gierda D S, Bae K T. *Radiology* 1999; 210:829-834; Quinn A D, O'Hare N J, Wallis F J, et al. *J Comput Assist Tomogr* 1994; 18:634-636; Pena C S, Kaufman J A, Geller S C, et al. *J Comput Assist Tomogr* 1999; 23:23-24.). Furthermore, the short in vivo residence time of these agents would impose limitations on the size of the anatomic region that could be imaged optimally and would exclude them from being used in image-guidance applications due to their inability to provide prolonged contrast enhancement for the entire course of treatment (Saeed M, Wendland M F, Higgins C B. *J Magn Reson Imaging* 2000; 12:890-898).

A viable way to effectively deliver the required amount of contrast in each imaging modality and to prolong the presence of the agents in vivo is to employ carriers such as liposomes. Specifically, liposome-based systems have been evaluated for either encapsulating (Kao C Y, Hoffman E A, Beck K C, et al. *Acad Radiol* 2003; 10:475-483; Leike J U, Sachse A, Rupp K. *Invest Radiol* 2001; 36:303-308; Leander P, Hoglund P, Borseth A, et al. *Eur Radiol* 2001; 11:698-704; Schmiedl U P, Krause W, Leike J, et al. *Acad Radiol* 1999; 6:164-169; Spinazzi A, Ceriati S, Pianezzola P, et al. *Invest Radiol* 2000; 35:1-7; Petersein J, Franke B, Fouillet X, et al. *Invest Radiol* 1999; 34:401-409; Leander P, Hoglund P, Kloster Y, et al. *Acad Radiol* 1998; 5 Suppl 1:S6-8; discussion S28-30; Krause W, Leike J, Schuhmann-Giampieri G, et al.

*Acad Radiol* 1996; 3 Suppl 2:S235-237; Dick A, Adam G, Tacke J, et al. *Invest Radiol* 1996; 31:194-203; Revel D, Corot C, Carrillon Y, et al. *Invest Radiol* 1990; 25 Suppl 1:S95-97; Musu C, Felder E, Lamy B, et al. *Invest Radiol* 1988; 23 Suppl 1:S126-129; Zalutsky M R, Noska M A, Seltzer S E. *Invest Radiol* 1987; 22:141-147; Seltzer S E, Shulkin P M, Adams D F, et al. *AJR Am J Roentgenol* 1984; 143:575-579; Jendrasiak G L, Frey G D, Heim R C, Jr. *Invest Radiol* 1985; 20:995-1002; Torchilin V P. *Curr Pharm Biotechnol* 2000; 1:183-215; Schneider T, Sachse A, Robling G, Brandi M. *Int J Pharm* 1995; 117:1-12; Pauser S, Reszka R, Wagner S, et al. *Anticancer Drug Des* 1997; 12:125-135.) or chelating (Weissig V V, Babich J, Torchilin V V. *Colloids Surf B Biointerfaces* 2000; 18:293-299; Misselwitz B, Sachse A. *Acta Radiol Suppl* 1997; 412:51-55; Unger E, Needleman P, Cullis P, et al. *Invest Radiol* 1988; 23:928-932; Kabalka G, Buonocore E, Hubner K, et al. *Radiology* 1987; 163:255-258; Grant C W, Karlik S, Florio E. *Magn Reson Med* 1989; 11:236-243) single CT or MR signal modifying agents. Most of these liposome-based signal modifying agents have been explored for blood pool imaging due to the long in vivo circulation lifetimes that may be achieved for these carriers. Yet, liposomes have also been identified as suitable carriers for the delivery of agents to the lymphatic system since they have been shown to avoid aggregation at the site of injection and localize in lymph nodes (Nishioka Y, Yoshino H. *Adv Drug Deliv Rev.* 2001; 47:55-64; Moghimi S M, Rajabi-Siahboomi A R. *Prog Biphys Molec Biol.* 1996; 65:221-249; Oussoren C, Storm G. *Adv Drug Deliv Rev* 2001; 50:143-156). The potential use of liposome-based signal modifying agents for lymphatic imaging is worth noting as it is well-known that the lymph nodes are the primary site for the metastases of many cancers (Swartz M A. *Adv Drug Deliv Rev.* 2001; 50:3-20; Swartz M A, Skobe M. *Microsc Res Tech* 2001; 55:92-99.). Until recently, there were no available non-invasive methods for distinguishing between lymph nodes enlarged due to the presence of metastatic cancer cells and nodes enlarged due to inflammation, or for identifying cancerous nodes of normal size. With the advent of Combidex® (Advanced Magnetics, Inc. USA), lymph nodes can now be enhanced in MR, and metastatic nodes can be differentiated from normal or inflamed nodes based on morphology and changes in signal intensity between scans performed before and after signal modifying agent injection (Xiang Y, Wang J, Hussain S M, Krestin G P. *Eur Radiol.* 2001; 11:2319-2331). However no delivery system has been developed for prolonged co-localization in vivo of two or more signal modifying agent for multiple medical imaging.

SUMMARY OF THE INVENTION

In a broad aspect of the invention there is provided signal modifying compositions for medical imaging comprising a carrier and signal modifying agents specific for two or more imaging modalities. In a preferred embodiment the compositions are characterized by retention efficiency, with respect of the signal modifying agents, that enables prolonged contrast imaging without depletion of the signal modifying agent from the carrier. The carriers of the present invention are lipid based or polymer based the physico-chemical properties of which can be modified to entrap or chelate different signal modifying agents and mixtures thereof and to target specific organs or tumors within a mammal.

The co-localization of imaging modalities specific signal modifying agents in a carrier advantageously enables the registration of images obtained from different imaging modalities. The registration can be exploited to refine diagnosis, design of therapeutic regimen, follow the progress of therapy such as radiation therapy and optimize contrast enhancement.

Thus, in one aspect, there is provided an image signal modifier composition for imaging of a biological tissue, the composition comprising: two or more signal modifying agents, each of the agent being specific for at least one imaging modality; and a carrier comprising the two or more signal modifying agents and wherein the carrier is capable of retaining a sufficient amount of the agents for a time sufficient to acquire imaging data using the composition.

The signal modifying agents are specific for imaging modalities selected from but not limited to magnetic resonance imaging (MRI), X-ray, ultrasound (US), positron emission tomography (PET), computed tomography (CT), autoradiography, single-photon emission computed tomography (SPECT), fluoroscopy, optical imaging, fluorescence imaging and bioluminescence imaging.

In a further aspect, the carrier is a lipid-based carrier such as a liposome or a micelle.

In an embodiment of the invention the composition can be targeted to a desired location within a subject or within a tissue. This can be achieved through control of the carrier physico-chemical properties or by inserting one or more recognition molecules such as antibodies, receptors/ligands, carbohydrates, proteins and peptide fragments.

In another embodiment the may comprise a therapeutic agent such as anticancer, antimicrobial, antifungal and antiviral agents.

In yet another aspect of the invention the there is also provided a method for imaging one or more region of interest in a mammal the method comprising: administering to the mammal a signal modifier composition waiting for a time sufficient for the composition to reach the region of interest; and obtaining an image of the one or more region of interest.

There is also provided a method for registering images obtained from two or more imaging modalities the method comprising: administering to a mammal a signal modifier composition, each agent being specific for at least one of the at least two or more imaging modalities; obtaining an image of one or more region of interest in the mammal using each of the at least two or more imaging modalities; and comparing the images obtained in b) to derive complementary information from the one or more region of interest.

In the present description by signal modifier or signal modifying it is meant that the signal obtained with a particular imaging modality is modified by an agent. Typically the agent is a signal enhancing agent (contrast agent) but the agent may also provide for signal attenuation or any other form of signal modification so as to provide a desired effect on the image.

By biological tissue or tissue it is meant any part of an animal, such as a mammal, including but not limited to organs, vessels, blood, breast tissue, muscular tissue, bones and the like.

By retaining or retention efficiency it is meant the capacity of a carrier to prevent leakage of a signal modifier agent out of the carrier.

By targeting it is meant the preferential accumulation of the compositions of the present invention in a given organ or anatomical structure or tissue, including cell populations. By active targeting it is meant that a target binding molecule, specific for a molecule in the target, is incorporated in (or associated with) the composition. Examples comprise antibodies and receptor/ligand pairs. Passive targeting refers to preferential distribution of the composition due to its physico-chemical properties.

BRIEF DESCRIPTION OF THE DRAWINGS

Further features and advantages of the present invention will become apparent from the following detailed description, taken in combination with the appended drawings, in which.

|   | [iodine] (mg/mL) | [gadolinium] (mg/mL) |
|---|---|---|
| A | 16.98 | 3.55 |
| B | 8.49 | 1.77 |
| C | 1.70 | 0.35 |
| D | 0.17 | 0.04 |
| E | 0.07 | 0.02 |

FIG. 6 (a) CT (2.5 mm slice thickness, 120 kV, 300 mA and 15.2 cm FOV) attenuation in HU as a function of signal modifying agent concentration in mmol/L; although gadolinium has CT attenuation properties, iodine provides more effective CT enhancement. (b) Differential signal intensity (with respect to water) in MRI (400 ms TR, 9 ms TE, 3 mm slice thickness, 19.9 cm FOV and 256×192 image carrier) as a function of increasing gadolinium and iodine concentrations; symbols represent liposome encapsulated agents (■), free Iohexyl and Gadoteridol (▲), free Gadoteridol (●) and free Iohexyl (▼);

FIG. 7 (a) 1/T1 relaxation rate and (b) 1/T2 relaxation rate as a function of gadolinium (Gd) and iodine (I) concentration obtained at 20° C. with a 1.5 T, 20-cm-bore superconducting magnet controlled by an SMIS spectroscopy console; Encapsulation of Gadoteridol greatly reduces both the $r_1$ and $r_2$ of the gadolinium atoms;

|   | $r_1$ ($s^{-1}mmol^{-1}L$) | $r_2$ ($s^{-1}mmol^{-1}L$) |
|---|---|---|
| (▲) Free Gadoteridol | 5.14 ± 0.06 | 6.21 ± 0.08 |
| (●) Free Gadoteridol and Iohexol (1:29 mole ratio of Gd to I) | 6.38 ± 0.16 | 7.83 ± 0.20 |
| (▲) Free Iohexol (x-axis = [I] in mmol/L) | 0.00 ± 0.00 | 0.01 ± 0.01 |
| (▼) Liposome encapsulated agents | 1.23 ± 0.02 | 1.46 ± 0.02 |

Figure 8:
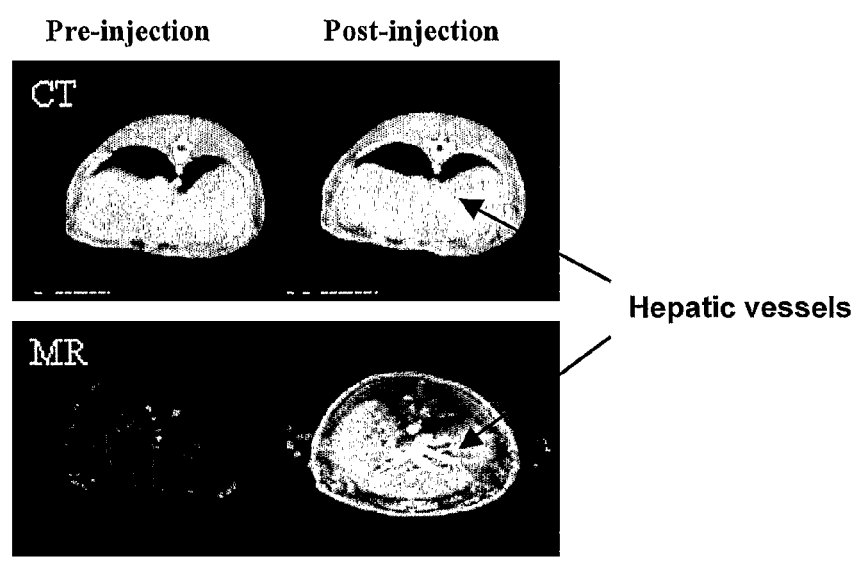
Figure 9:
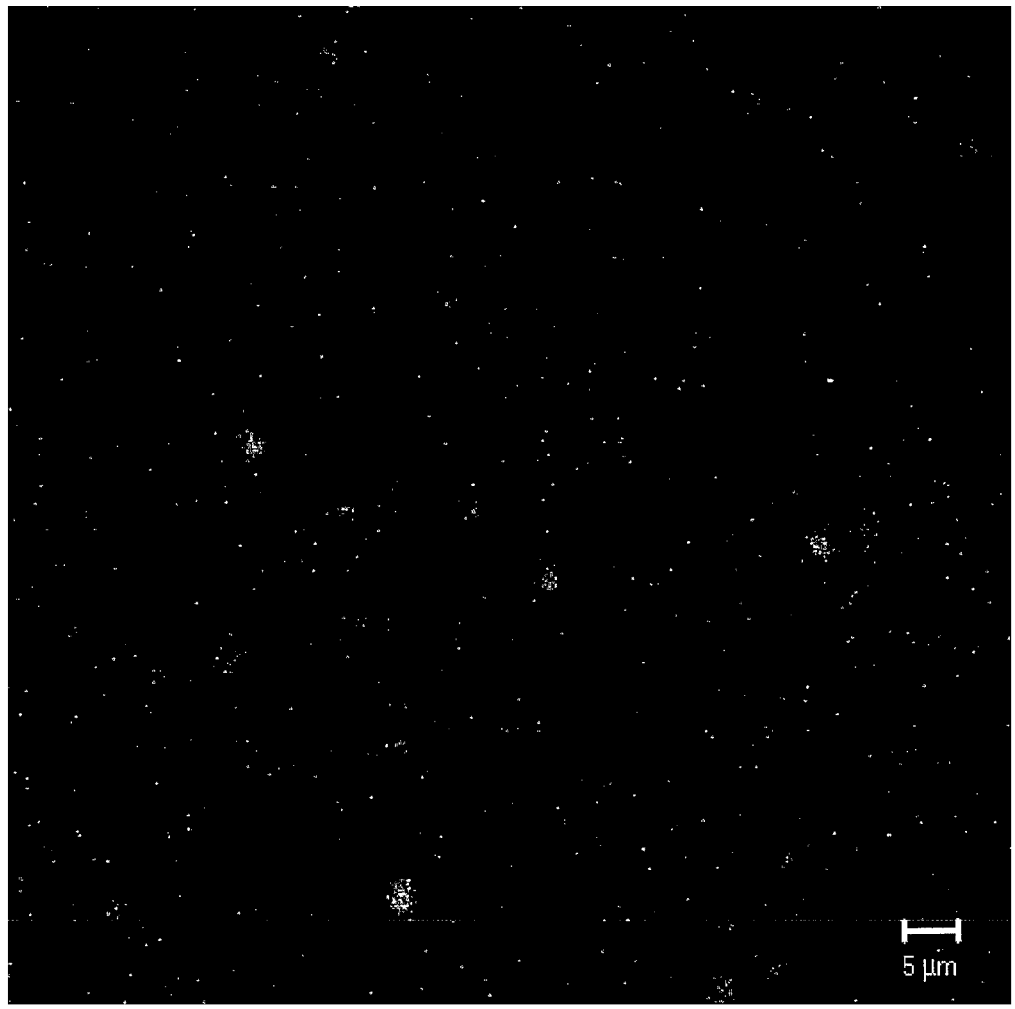
Figure 11A:
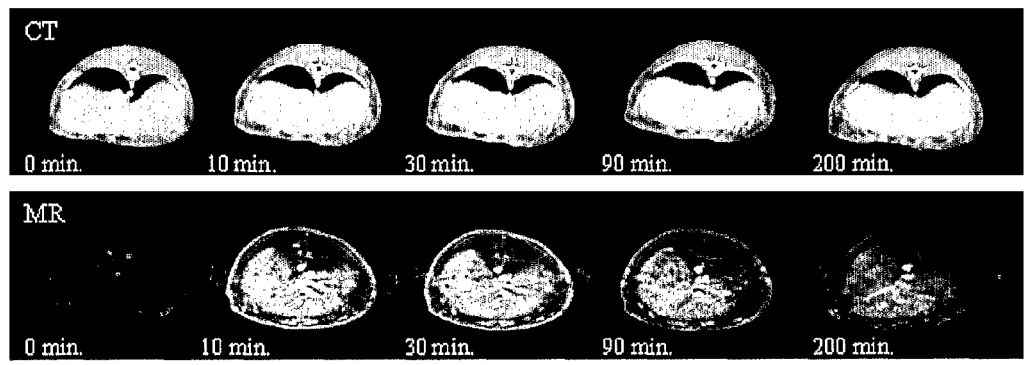
Figure 12:
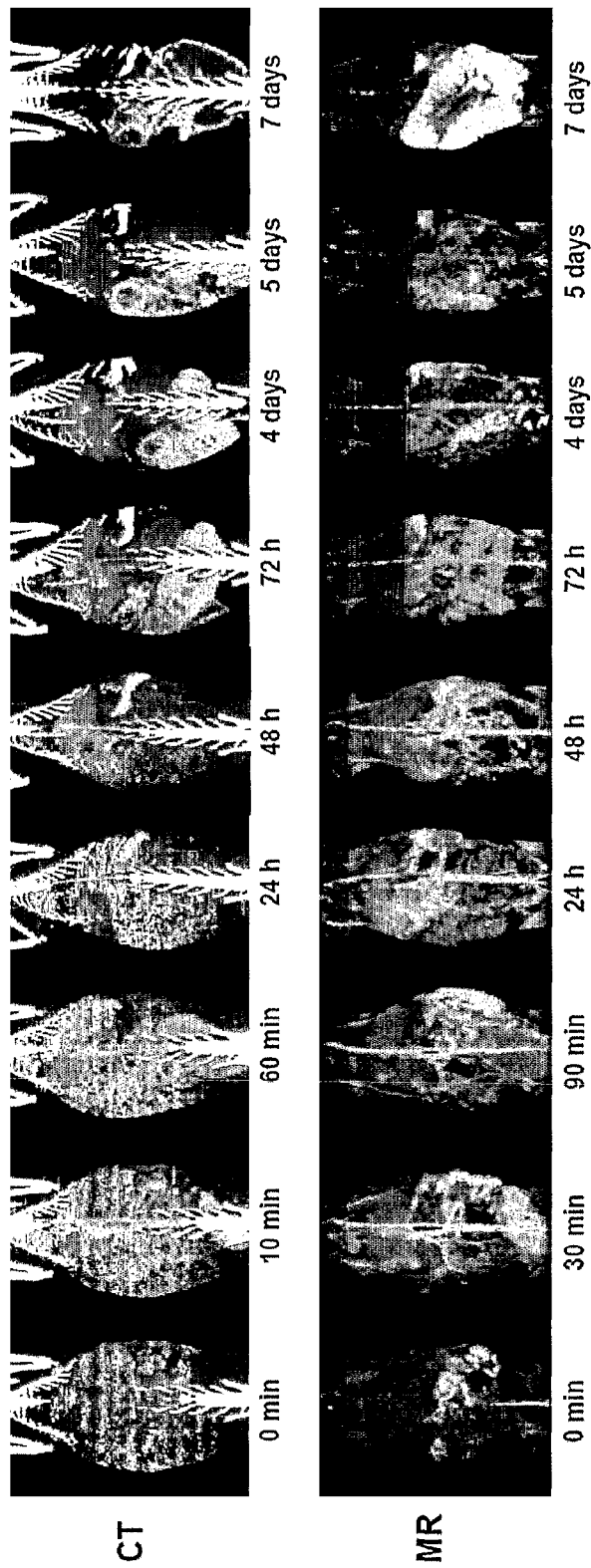
Figure 13:
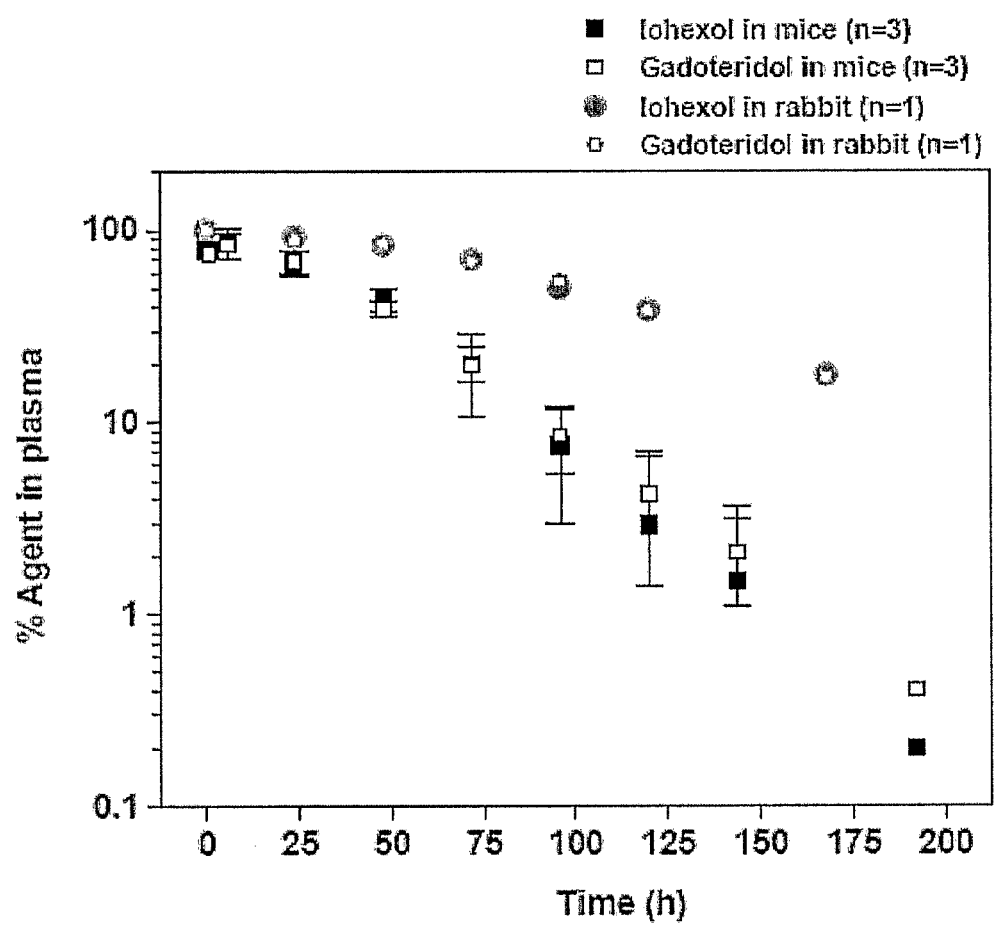
Figure 14:
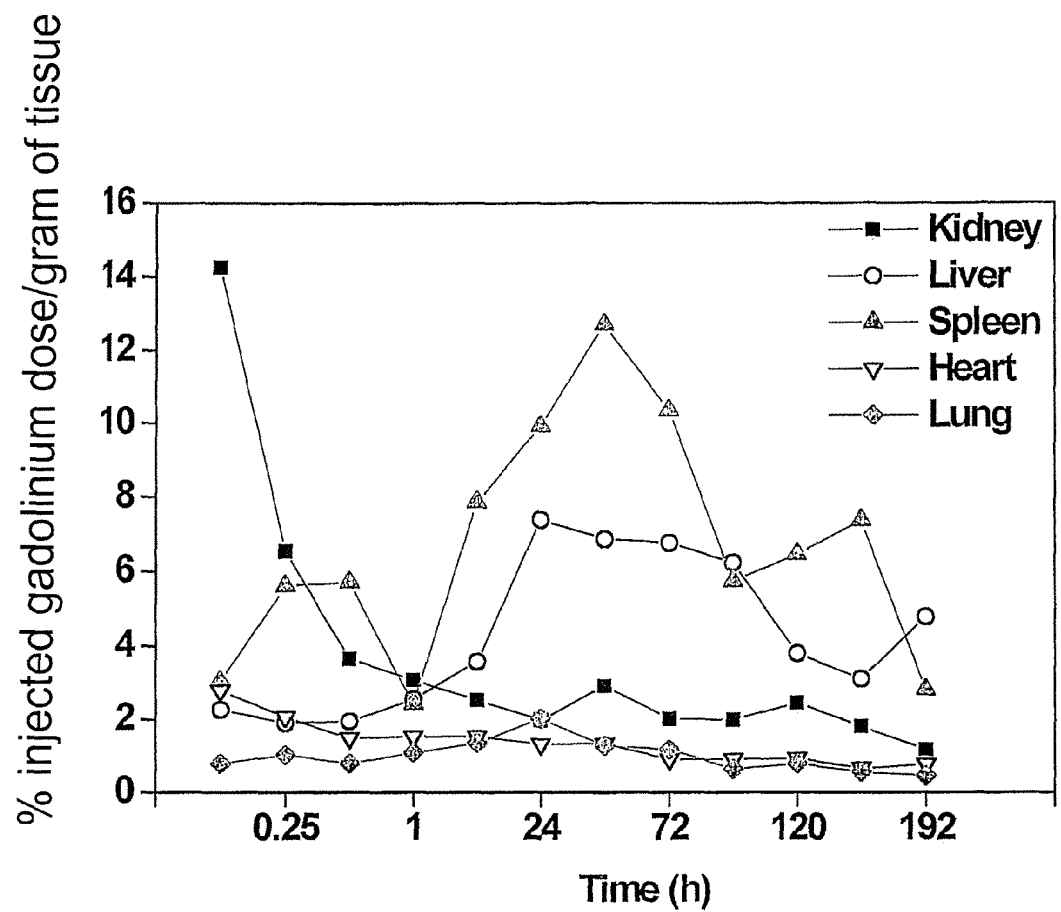
Figure 15:
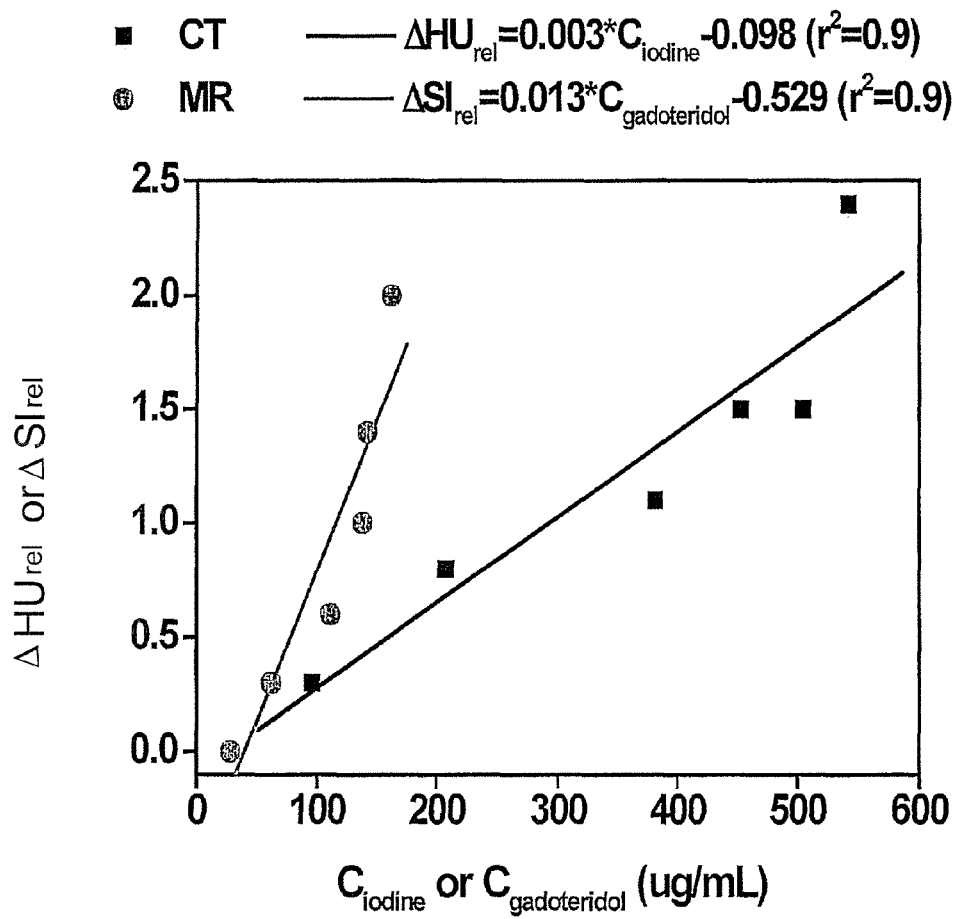

FIG. 8 is a liver cross-section images from a rabbit, before and after injection of signal modifying agent, in CT and MR;

FIG. 9 is a confocal microscopy image of a liposome formulation containing DPPC/Cholesterol/DSPEPEG/DPPE-NDB 1 (54.5/40/5/0.5 mole ratios) encapsulating iohexyl and gadoteridol; 1,2-dipalmitoyl-sn-glycero-3-phosphoethanolamine-N-(7-nitro-2-1,3-benzoxadiaxol-4-yl), the excitation wavelength is 460 nm and the emission wavelength is 534 nm; this liposome formulation is suitable for CT, MR and optical imaging;

FIG. 10 is a graphic of a relative signal enhancement of blood (aorta), liver (parenchyma) and kidney (medulla and cortex) up to 200 minutes following intravenous administration of the liposome-based signal modifying agent in (a) CT and (b) MR;

FIG. 11 is (a) CT and MR liver cross section scans of a 2.1 kg white New Zealand rabbit obtained before (0 min.) and after (10, 30, 90 and 200 minutes) signal modifying agent injection. Note the visual contrast enhancement obtained in the aorta, the hepatic vessels, and the liver parenchyma up to 3 hours and 20 minutes in both imaging modalities. (b) CT and MR cross section scans of the left kidney obtained before (0 min.) and after (10, 60, 120 and 200 minutes) signal modifying agent injection. Note the visual contrast enhancement obtained in the kidney. The same window level was used for pre- and post-injection images;

FIG. 12 are 3D maximum intensity projection images (anterior view) of the rabbit in CT (120 kV, 200 mA) and MR (3D FSPGR, TR/TE=9.8/4.3) before the injection of the contrast agent modified liposomes (0 minutes) and 48 hours and 168 hours post-injection (300 mg/kg of iodine and 16 mg/kg of gadolinium encapsulated in liposomes), the parallel visual enhancement seen in both CT and MR obtained in the major blood vessels, liver, spleen and intestines represents the liposome distribution over a 7-day period, the spine and part of the ribs of the rabbit have been masked in the CT image set for better soft tissue visualization;

FIG. 13 is a graphic of the percentage of the total injected CT (iohexyl, detected with HPLC at 245 nm wavelength) or MR agent (gadoteridol, detected with ICP-AES) remaining in mouse plasma (female Balb-C, 18-23 g, one mouse per time point) and rabbit plasma (female New Zealand White, 2 kg, same rabbit used for all time points) at specific time points following administration, the ratio of iodine to gadolinium is 13.9±3.0 in mice and 11.9±0.5 in the rabbit at all time points;

FIG. 14 is a liposome distribution estimated from the percentage of the injected gadolinium encapsulated in liposomes per gram of tissue (kidney, liver, spleen, heart and lung) over a 8-day period in female Balb-C mice; and FIG. 15 are relative signal differences measured in the rabbit aorta using CT and MR correlate linearly ($R^2$=0.9) with the iodine and gadoteridol concentrations detected in the rabbit plasma using HPLC and ICP-AES assays, respectively, the relative HU ($\Delta HU_{rel}$) was calculated as a function of the HU value found at the same anatomic location prior to the injection of the liposome sample ($\Delta HU_0$) as described in equation (1), similarly, the relative MR signal intensity ($\Delta SI_{rel}$) was calculated as a function of the pre-injection signal intensity value ($\Delta SI_0$) as described in equation (2).

$$\Delta HU_{rel} = \frac{(\Delta HU_{rel} - \Delta HU_0)}{\Delta HU_0} \quad \Delta SI_{rel} = \frac{(\Delta SI_{rel} - \Delta SI_0)}{\Delta SI_0} \quad (1)$$

DETAILED DESCRIPTION OF THE INVENTION

A novel approach is provided, in which image signal modifier compositions are designed to provide long-lasting image signals for accurate spatial registration over the course of therapy or diagnosis and between imaging-modalities used in the design and guidance of the therapy. Such a composition provides a unique platform for accurate design, image-guided delivery, and assessment of therapy.

Thus, there is provided compositions and methods for signal modification such as contrast enhancement in imaging modalities. In one aspect there is provided multimodal signal modifier compositions that comprise at least two signal modifying agents and a carrier, each signal modifying agent being specific for at least one imaging modality. The combination of the signal modifying agents enables the co-localization, within specific anatomical structures as part of biological tissues (organs, tumors and the like) of mammals (including humans), of the signal modifying agents which, in turn, allows acquisition of the images obtained by two (or more) imaging modalities and also allows for registration of the images. Such compositions may be used for imaging various organs and tissues as well as any tubule and vessel system in the body (i.e. blood vessels, hepatic vessels, renal vessels, and the lymphatics).

The multimodal signal modifier compositions of the present invention may be used with imaging modalities that are based on magnetic resonance, ultrasound, X-ray, optical, positron-emission, single-photon emission, radioactivity and the like provided that the signal modifying agents possess the required signal modifying properties as would be known to a person skilled in the art. For example in the case of magnetic resonance imaging (MRI) the signal modifying agent should possess magnetic properties (high relaxivity) capable of modifying the relaxation time of bulk water molecules. As another example, signal modifying agents for X-ray imaging should exhibit bulk attenuation characteristics. Signal modifying agents can possess properties that render them suitable for signal modification of more than one imaging modality. A carrier may comprise any combination of signal modifying agent. Non-limiting examples include: signal modifying agents for MRI/X-ray, MRI/optical, MRI/X-ray/optical, optical/PET, MRI/CT/optical, etc.

Signal modifying agents specific for each imaging modalities (CT, MR' radionuclide, optical) are well known in the art. Non-limiting examples of signal modifying agents include gadolinium, manganese and iron based agents (MRI), iodine based agent (CT), alpha, beta and positron emitting radiotracers (autoradiography, PET and SPECT), fluorophores (optical), and perfluorocarbons.

The multimodal signal modifier compositions of the present invention comprise a carrier having physico-chemical properties compatible with the retention of the signal modifying agents. Retention of the signal modifying agent molecules is desirable to prevent dispersion of the agent within the body and to prevent the depletion of the signal modifying agents from the carrier, which would reduce the signal intensity. Thus, effective retention results in prolonged in vivo contrast enhancement thereby avoiding the need for multiple administration over the course of image acquisition and allowing registration of images obtained over a period of time. In a preferred embodiment the carrier can retain between about 10 and 100% of the signal modifying agent over the course of imaging. In a more preferred embodiment this retention is of the order of about 80 to 100% and in an even more preferred embodiment the retention is above 90%. Thus the carrier should be sufficiently stable with respect to agents' retention so as to allow sufficient time for the composition to reach a region of interest an enable acquisition of imaging data. Furthermore the carrier should also remain in the tissue of interest for a time sufficient to allow acquisition of imaging data over a desired period of time. This period of time may depend on the information that is required, the nature of therapeutic regimens being applied, the progression of a disease and the like. The period of time may extend from a few minutes to several days.

Figure 1:
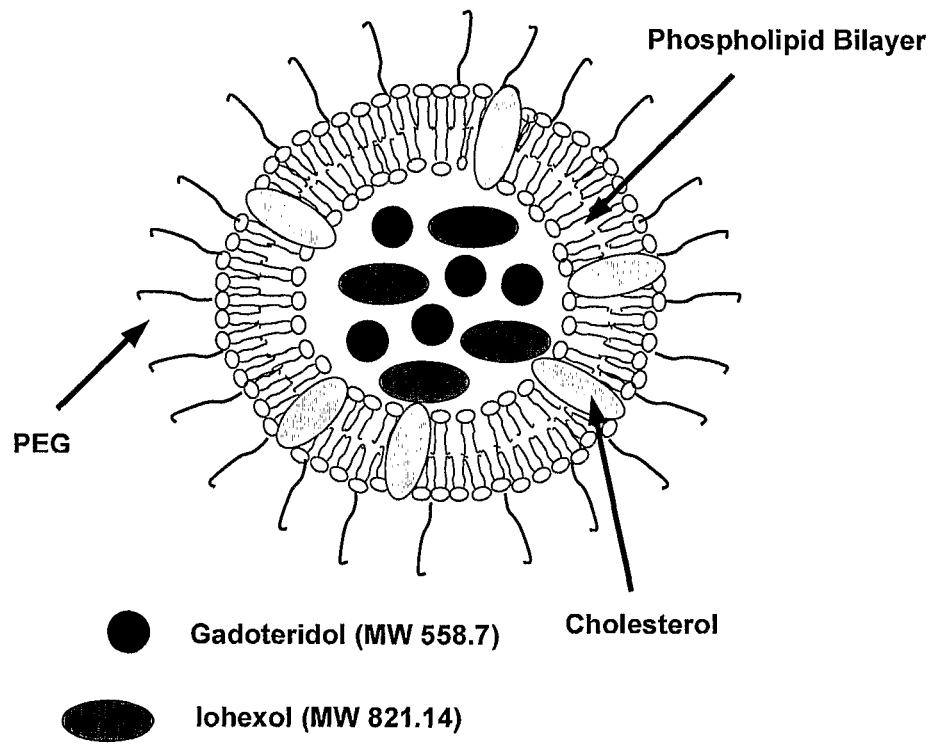
FIG. 1 is a schematic representation of the liposome-based signal modifying agent system.

In one embodiment, the carrier is used to entrap (encapsulate) the signal modifying agents and in a preferred embodiment the carrier consists of a lipid based carrier such as lipid micelles, unilamellar (see FIG. 1) and multilamellar vesicles such as liposomes.

Lipid micelles have small diameters: 8 nm-50 nm and are made of a single lipid layer and are therefore suitable for encapsulating hydrophobic signal modifying agents, such as Perfluorooctyl bromide (perflubron).

The composition of the carrier may be adjusted as required in order to optimize the loading capacity, release kinetic profiles for each agent, and the stability of the overall system. For example, for a lipid-based carrier such as liposome, it is well known that the membrane fluidity may affect the permeability of certain compounds. The molecular characteristics of the membrane that are known to affect fluidity include, but are not limited to, lipid saturation, fatty acid chain length, charge of the polar head of the lipids, cholesterol content and the like. It will be appreciated that encapsulation of the signal modifying agents should not substantially affect their signal modifying (for example contrast enhancing) properties. In this respect, the composition of the carrier preferably minimizes the leakage of the encapsulated agents and optimizes the contrast enhancement abilities of the encapsulated agents. For example, bulk water accessibility to signal modifying agents should be considered when designing a carrier composition for MRI. It will also be appreciated that the signal modifying agents may be chosen to be compatible with a given carrier composition. For example, while a signal modifying agent may be prone to leak out of a liposome having a given lipid composition, a different signal modifying agent may be less so for the same lipid composition.

In a preferred embodiment the lipid composition of the lipid based carrier comprises a neutral lipid, cholesterol and polyethylene glycol ($PEG_{2000}$)-phosphatidylethanolamine (PE).

A second approach to couple the signal modifying agent(s) to the carrier involves chelation or covalent linking of at least one of the signal modifying agents to the outer surface of the carrier (such as a liposome). This approach can, for example, increase the access to bulk water thereby enhancing the efficiency of MR signal modifying agents. This strategy also maximizes the entire internal aqueous volume of the carrier as cargo space for the other or several other signal modifying agents. For example, radionuclides can be chelated on derivatized lipids. Hydrophilic agents can be chelated (see below) onto their outer surface along with Poly-ethylene glycol (PEG) groups. Chelators may comprise EDTA, DTPA, TETA, HYNIC and other structurally related analogues. It will be appreciated that coupling of signal modifying agents may comprise high affinity linker molecules such as avidin-biotin. The signal modifying agent may also be covalently linked to the carrier. For example fluorophore can be thus linked to lipid molecules that can in turn be incorporated in a lipid carrier.

The encapsulation (or chelation) of small molecular weight signal modifying agents into a macromolecule carrier (i.e. liposome) significantly reduces their in vivo volume distribution, prolongs their in vivo circulation time and increases their ability to accumulate in specific locations within the body such as in tumors. It will be appreciated that accumulation may take place through passive or active targeting mechanisms. With respect to active targeting mechanisms, techniques such as antibody coating or attachment of specific cellular receptors/ligands (such as Epidermal Growth Factor, EGF and its receptor, EGFR) onto the surface of the carrier or in association with polymeric matrices may be used as would be known to those skilled in the art. Non-limiting examples also include small molecules (Saul J M, Annapragada A, Natarajan J V, et al. J Control Release 2003; 92:49-67; Lee R J, Low P S. Biochim Biophys Acta 1995; 1233:134-144; Lee R J, Low P S. J Biol Chem 1994; 269:3198-3204.), sugar (carbohydrates) molecules (Spanjer H H, Scherphof G L. Biochim Biophys Acta 1983; 734:40-47; Spanjer H H, Morselt H, Scherphof G L. Biochim Biophys Acta 1984; 774:49-55; Banerjee G, Nandi G, Mahato S B, et al. J Antimicrob Chemother 1996; 38:145-150; Luciani A, Olivier J C, Clement O, et al. Radiology 2004; 231:135-142.), serum proteins (Afzelius P, Demant E J, Hansen G H, et al. Biochim Biophys Acta 1989; 979:231-238; Brown P M, Silvius J R. Biochim Biophys Acta 1990; 1023:341-351; Lundberg B, Hong K, Papahadjopoulos D. Biochim Biophys Acta 1993; 1149:305-312.) and antibodies (Heath T D, Montgomery J A, Piper J R, et al. Proc Natl Acad Sci USA 1983; 80:1377-1381; Debs R J, Heath T D, Papahadjopoulos D. Biochim Biophys Acta 1987; 901:183-190; Matthay K K, Abai A M, Cobb S, et al. Cancer Res 1989; 49:4879-4886; Maruyama K, Holmberg E, Kennel S J, et al. J Pharm Sci 1990; 79:978-984; Allen T M, Ahmad I, Lopes de Menezes D E, et al. Biochem Soc Trans 1995; 23:1073-1079) or antibody fragments (Kirpotin D, Park J W, Hong K, et al. Biochemistry 1997; 36:66-75; Park J W, Hong K, Carter P, et al. Proc Natl Acad Sci USA 1995; 92:1327-1331.). Consequently, nonspecific toxicity can be greatly reduced (i.e. renal-toxicity often associated with iodine-based signal modifying agents) and specific imaging efficacy increased.

It will be appreciated that active targeting can be tested for example by injecting a signal modifier composition comprising a target binding molecule for which the target is known and measuring the amount of the composition reaching the target. The target may be an extrinsic target, that is to say, the target can be incorporated in an animal at a predetermined location such as a tumor expressing a particular receptor for which the ligand is known and introduced in the composition.

The in vivo behavior of carrier such as distribution and clearance kinetics is highly dependent on the their size, composition, surface characteristics and route of administration. The size distribution of the carrier used in the present invention is between 30 and 1000 nm, preferably between 30 and 500 nm and most preferably between 50 and 150 nm.

Preferably the composition of the present invention will remain in circulation or in an organ for an extended period of time. Preferably the composition will remain for several hours and more preferably for several days.

It will be appreciated that the signal modifying agents may be separately encapsulated in or associated with carriers of the same sizes, membrane compositions and surface characteristics, conferring similar pharmacokinetic properties enabling the co-localization within tissues. However, the carriers may also differ in their properties and their pharmacokinetics properties may therefore be different. Insofar as the differences in the pharmacokinetics are known or measured, they may be exploited for differential localization within regions of interests in the body.

I will be appreciated that the carriers of the invention may comprise polymer-based material.

The contrast enhancing compositions of the present invention may also comprise therapeutic agents for delivery in organs/tissues/cells targeted by the carriers. The combination of the signal modifying agents and therapeutic agents advantageously allows the monitoring of the in-vivo distribution of therapeutic agent at least at the stage of agent delivery and the biological effects of the therapeutic agent (such as tumor shrinkage, etc.). Examples of therapeutic agents include anti-cancer drugs such as anthracyclines (i.e. doxorubicin, daunorubicin), vinca alkaloids (i.e. vincristine, navelbine) and other drugs such as 5-FU, ara-C, camptothecin analogues (i.e. lurtotecan, topotecan), platinum-based compounds (i.e. cisplatin, carboplatin), anti-fungal agents such as amphotericin B, anti-bacterial agents such as antibiotics (minocycline, doxycycline and the like), anti-viral agents and other therapeutic agents as would be know to those skilled in the art.

In another aspect of the invention, there is provided a method for imaging biological tissue using the image signal modifier composition of the invention. The image signal modifier composition is administered to a subject and one or more images can be obtained with one or more imaging modality for which the composition provides signal modification such as contrast enhancement. It will be appreciated that a time sufficient to allow distribution of the signal modifier composition within the subject may be allowed prior to acquisition of the image.

The kinetics of distribution of the composition may depend on several factors such as the nature of the composition itself, the mode of injection and the like. Determination of the kinetics can be achieved, for example, by acquiring images at different times after administration of the composition.

The properties of the signal modifying agents can also influence the duration of the signal modification. Thus it will be appreciated that the stability of the signal modifying agent may influence the quality of the image as well as the available window of time to acquire imaging data. The half-life of radionuclides and lifetime of fluorophores are examples of stability characteristics that should be taken in consideration. It will be further appreciated that the optimal concentration of the signal modifying agents within the carrier depends on the type of imaging being performed, the region of interest being imaged, the duration of the imaging protocol, the stability of the agent, the characteristics of the agents such as specific activity, quantum efficiency and the like, and any other factor as would be known to the person skilled in the art.

Image acquisition using the signal modifier composition of the invention may be used for the detection of abnormalities within biological tissues. By abnormalities it is meant anatomical structures not normally present in a tissue such a tumors for example.

In another aspect of the invention there is provided a method for the registration of images obtained by two or more imaging modalities using the composition of the present invention. A multimodal signal modifier composition advantageously co-localize the signal modifying agents thereby enabling the correlation of images obtained using two or more imaging modalities. Medical images can be divided in two types. Structural (anatomical) images and functional images. Functional and molecular imaging using single photon emission computed tomography (SPECT), positron emission tomography (PET) and optical imaging is extremely valuable in the diagnosis of various disorders. The method for the registration of images according to the present invention allows the correlation between structural (anatomical), functional and molecular images or a combination or a combination thereof thereby providing complementary information of a region of interest.

Furthermore, the long in vivo residence time of the compositions of the present invention allows for multiple scans to be obtained from one or more imaging modalities following a single injection. This in turn enables the direct correlation of the signals obtained in distinct imaging modalities and allow for correct correspondence between different regions in the image. Thus multimodal signal modifying compositions may also assist in the development of novel image registration techniques, such as biomechanical based registration, which can take advantage of the clear definition of organ boundaries and substructures enhanced in each modality. In addition to improving the performance of image registration techniques, this signal modifying agent may also enhance the ability to identify naturally occurring fiducial points (i.e. vessel bifurcations) used to verify the accuracy of registration techniques.

Multimodal image registration and fusion are valuable tools for both diagnosis and treatment planning because the combination of information from multiple sources can be applied to enhance conspicuity of relevant data with respect to irrelevant information. Thus, image acquisition and registration can contribute to the design, implementation and assessment of therapeutic regimens. For example, knowledge acquired from the spatio-temporal distribution of a therapeutic compound included in the carrier can be exploited to determine appropriate doses, frequency of administration, mode of administration and the like. In particular the composition and method of the invention can be useful to establish therapeutic regimens for, but not limited to, cancer treatment. For example, combination of MRI and CT images may advantageously be used for establishing radiation therapy protocols. The progress of the therapy may also be followed by acquiring images using more than one imaging modality over a given time period during and after the therapy.

The composition of the present invention can also be used as a fiducial marker. A fiducial marker is defined as a point or structure of reference (static or not). The composition of the invention is able to act as a moving structure of reference for multiple detectors (i.e. CT, MR, optical etc.) with a limited lifetime (hours). The advantage of using our agent as a multimodal fiducial marker for short-term applications is that it is much less invasive (and less painful) than implanting fiducial markers of any size. In addition, repeated injections of the agent could allow for use as a long-term fiducial marker.

Through size and composition variations (i.e. mixture of known ratios of one or more carrier of different sizes), differential in vivo circulation, accumulation and clearance kinetics can be achieved in order to tailor the agent for different imaging applications at the same time and/or at different times. In this respect, the pharmacokinetics of a particular composition may be adjusted so as to target organs/tissues/cells or tumors that require contrast enhancement. If necessary several different contrast enhancement compositions each having different pharmacokinetic properties can be used to optimize contrast enhancement of one or more desired regions of interest in a modality specific manner.

The composition of the invention is preferably administered to a subject using a pharmaceutical acceptable diluent compatible with the preservation of the physico-chemical properties of the composition such as saline solutions. The mode of administration may comprise intravenous, peritoneal, sub-cutaneous, intra muscular or other modes as would be known to the skilled in the art.

The composition of the invention may be provided in kits comprising the carrier formulation and signal modifying agents such as to provide a multi-modal image signal modifier composition. The kits may also comprise a pharmaceutically acceptable diluent and therapeutic agents.

Example 1

Radionuclide imaging in accordance with the method and composition described above may involve incorporation of derivatized lipids that can chelate the radiometals $^{99m}Tc$ and $^{111}In$ for SPECT imaging and $^{64}Cu$ for PET. These radionuclides are readily available from a generator system ($^{99}Mo/^{99m}Tc$; Bristol-Myers-Squibb) or can be purchased from MDS-Nordion Inc. ($^{111}In$ and $^{64}Cu$). PE lipid can be derivatized at the headgroup with HYNIC for labeling with $^{99m}Tc$; DTPA for labeling with $^{111}In$; or with TETA for labeling with $^{64}Cu$. These bifunctional chelators are all commercially available from Macrocyclics Inc. Unilamellar liposomes can be prepared using established methods based on high-pressure extrusion and sonication. The labeled liposomes can be formed from the newly synthesized chelator-modified PE and the mixture of lipids originally employed in the liposome formulation. Following preparation, liposomes containing the chelator-modified PE lipid can be incubated with $^{99m}Tc$, $^{111}In$, $^{64}Cu$ or combination thereof in an appropriate labeling buffer for 30 minutes, then the unbound radioactivity can be removed by size-exclusion chromatography.

Example 2

Methods and Materials

Materials

The components of liposomes: 1,2-Dipalmitoyl-sn-Glycero-3-Phosphocholine (DPPC, M.W. 734), Cholesterol (CH, M.W. 387) and 1,2-Distearoyl-sn-Glycero-3-Phosphoethanolamine-N-[Poly(ethylene glycol)2000] ($PEG_{2000}DSPE$, M.W. 2774) were purchased from Northern Lipids Inc. (Vancouver, British Columbia, Canada). The CT signal modifying agent, Omnipaque® was obtained from Nycomed Imaging AS, Oslo, Norway. Omnipaque® (300 mg/mL of Iodine) contains iohexyl (M.W. 821.14), an iodinated, water-soluble, non-ionic monomeric contrast medium. The MR signal modifying agent used was ProHance® from Bracco Diagnostics Inc. (Princeton, N.J., USA). ProHance® (78.6 mg/mL of gadolinium) contains gadoteridol (M.W. 558.7), a non-ionic gadolinium complex of 10-(2-hydroxy-propyl)-1,4,7,10-tetraazacyclododecane-1,4,7-triacetic acid.

Preparation of Liposome Formulations

Lipid mixtures (200 mmol/L) of DPPC, cholesterol and $PEG_{2000}DSPE$ in 55:40:5 percent mole ratios were dissolved in ethanol at 70° C. The lipid-ethanol solution was then hydrated at 70° C. with Omnipaque® and Prohance®. The initial ethanol content was $10\%_{vol}$. The resulting multilamellar vesicles were then extruded at 70° C. with a 10 mL Lipex™ Extruder (Northern Lipids Inc., Vancouver, British Columbia, Canada). Specifically, the samples were first extruded 5 times with two stacked polycarbonate membranes of 0.2 µm pore size (Nucleopore® Track-Etch Membrane, Whatman Inc., Clifton, N.J., USA) and subsequently 5 times with two stacked polycarbonate membranes of 0.08 µm pore size.

Physico-Chemical Characterization Liposome Formulations

Liposome Size and Morphology

The size of liposomes was measured by dynamic light scattering (DLS) at 25° C. using a DynaPro DLS (Protein Solutions, Charlottesville, Va., USA). Liposome morphology was studied by transmission electron microscopy (TEM) with a Hitachi 7000 microscope operating at an acceleration voltage of 80 kV. The liposome sample was first diluted in distilled water and then mixed with phosphotungstic acid (PTA) in a 1:1 volume ratio. The sample solutions were then deposited onto negatively charged copper grids that had been pre-coated with carbon.

Evaluation of Loading Efficiency, In Vitro Stability and In Vitro Release Kinetics Following liposome preparation (the average molecular weight of each liposome was estimated to be $5\times10^8$ g/mol) the unencapsulated agent was removed by membrane dialysis. Specifically, 1 mL of the liposome sample was placed in an 8000 molecular weight cut-off (MWCO) dialysis bag suspended in 250 mL of HEPES buffer saline (HBS) and left to stir for 8 hours. The liposomes were then ruptured using a 10-fold volume excess of ethanol in order to measure the concentration of encapsulated agents. The iodine concentration was determined using a UV assay with detection at a wavelength of 245 nm (He$\lambda$ios $\gamma$, Spectronic Unicam, Mass., USA). The gadolinium concentration was determined using an assay based on inductively coupled plasma atomic emission spectrometry (ICP-AES Optima 3000DV, Perkin Elmer, Mass., USA). The encapsulation efficiency of the agents was calculated using the following equation:

$$\% \text{ encapsulation efficiency} = \frac{\text{amount of agent encapsulated}}{\text{amount of agent added during preparation}} \cdot 100$$

The in vitro release kinetic profile for both agents was assessed by the dialysis method (Liu J, Xiao Y, Allen C. *J Pharm Sci* 2004; 93:132-143.). In short, 1 mL of the liposome sample was placed in a dialysis bag (MWCO 8000) suspended in 250 mL of HBS and incubated at 4° C. or 37° C. At specific time points, 5 mL of the dialysate was removed for measurement of the iodine and gadolinium concentrations and 5 mL of fresh HBS was added in order to maintain constant volume. The stability of the liposomes was assessed by measuring the size of liposomes at specific time points during the incubation period.

In Vitro CT and MR Imaging

In vitro contrast efficacy was determined by imaging the liposome formulated signal modifying agents at varying concentrations in both CT and MR, using a multimodal imaging phantom. To minimize the amount of agent leakage from liposomes, in vitro imaging scans were performed immediately following the removal of free agents by dialysis. CT scanning was performed using a GE LightSpeed Plus 4-detector helical scanner (General Electric Medical Systems, Milwaukee, Wis., USA) with the following scan parameters: 2.5 mm slice thickness, 120 kV, 300 mA and 15.2×15.2 cm field of view (FOV). The mean attenuation in Hounsfield units was measured using circular regions of interest (ROI). Attenuation values were then plotted against signal modifying agent concentrations using linear regression analysis.

MR imaging was performed with a 1.5 Tesla GE Signa TwinSpeed MR scanner and a head coil (General Electric Medical Systems, Milwaukee, Wis., USA). The phantom and the vials were filled to capacity to minimize air-induced susceptibility artefacts. Scans were produced using a T1 weighted spin echo sequence with a repetition time (TR) of 400 ms, an echo time (TE) of 9 ms, a slice thickness of 3 mm, a FOV of 1 9.9×19.9 cm and an image carrier of 256×192 pixels. The relative signal intensity was taken over the ROI. Solutions of free signal modifying agents were also imaged as controls in both modalities.

In Vitro Relaxometry

All in vitro relaxometry measurements were performed at 20° C. on a 1.5 Tesla, 20-cm-bore superconducting magnet (Nalorac Cryogenics Corp., Martinez, Calif.) controlled by an SMIS spectroscopy console (SMIS, Surrey, UK). The $T_1$ relaxation time data were acquired using an inversion recovery (IR) sequence (45) with 35 inversion recovery time (TI) values logarithmically spaced from 1 to 32000 ms. A 10 second delay was given between each acquisition and the next inversion pulse. The $T_2$ relaxation time data were acquired using a CPMG sequence (Carr H, Purcell E. *Phys Rev* 1954; 94:630-638; Meiboom S, Gill S. 1958; 29:668-691.) with TE/TR=$\frac{1}{10000}$ ms. For every measurement 2000 even echoes were sampled with 8 averages. The effects of any residual transverse magnetization following the off-resonance irradiation was removed by phase-cycling the $\pi/2$ pulse (−x/x).

The $T_1$ relaxation data were analyzed assuming monoexponential behaviour $$\left(S = M_0 \cdot \left(1 - 2 \cdot e^{-\frac{t}{T_1}}\right)\right),$$

where S is the signal observed, $M_0$ is the magnetization at equilibrium, t is time and $T_1$ is the longitudinal relaxation time). All $T_2$ decay data were plotted to a one component $T_2$ model with a Gaussian fit on a logarithmic time scale. The $r_1$ and $r_2$ values were calculated from linear regression analysis of $1/T_1$ and $1/T_2$ relaxation rates versus gadolinium concentration.

Results

Physico-Chemical Characterization of Liposome Formulation

Figure 2A:
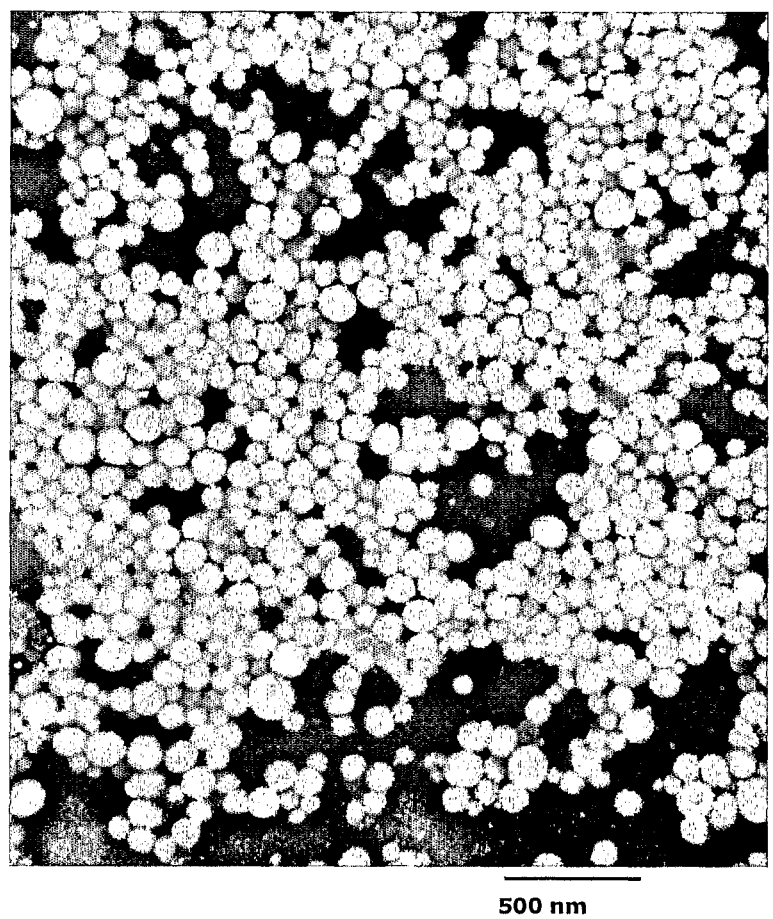
FIG. 2 is a transmission electron micrograph of the negatively stained dual-agent containing liposomes at (a) 40000 magnification and (b) 80000 magnification.
Figure 2B:
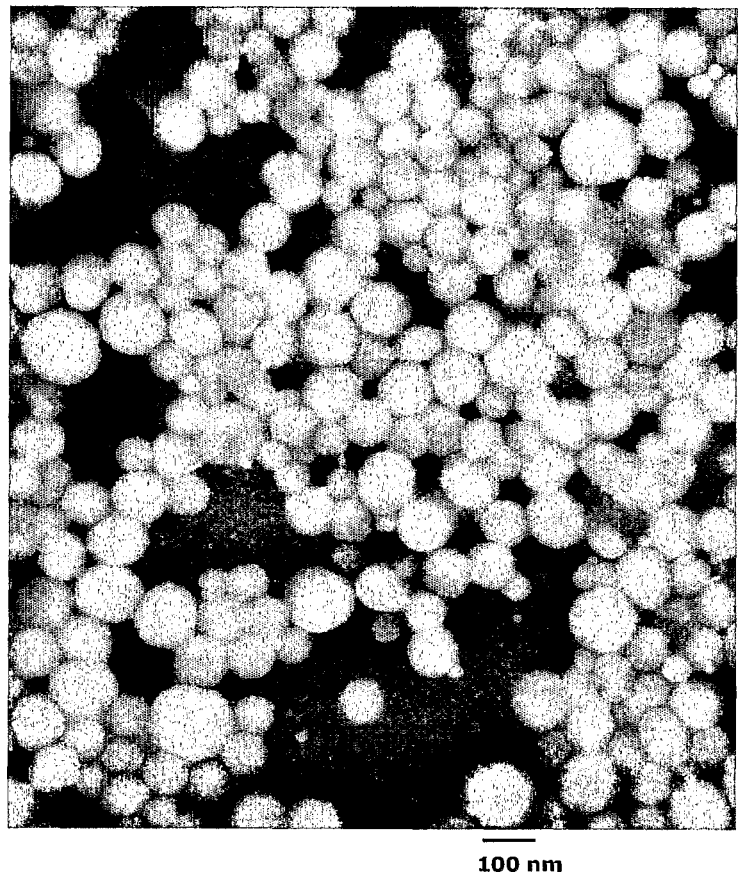

The prepared liposome formulation resulted in vesicles having a spherical morphology (FIG. 2) and a mean diameter of 74.4±3.3 nm. Table 1 summarizes the agent loading properties of the liposome formulation. The average loading efficiency (n=8) achieved for iohexyl was 19.6±2.8% (26.5±3.8 mg/mL iodine loaded, approximately $1.3\times10^6$ iodine molecules per liposome), which represents an agent to lipid ratio of approximately 0.2:1 (wt:wt). The average loading efficiency (n=8) attained for gadoteridol was 18.6±4.4% (6.6±1.5 mg/mL gadolinium loaded, approximately $1.3\times10^5$ gadolinium molecules encapsulated in one liposome), which represents an agent to lipid ratio of approximately 0.05:1 (wt:wt).

TABLE 1

| Diameter (nm) | Iodine added (mg/mL) | Iodine loaded (mg/mL) | Iodine loading efficiency (%) | Gadolinium added (mg/mL) | Gadolinium loaded (mg/mL) | Gadolinium loading efficiency (%) |
|---|---|---|---|---|---|---|
| 74.4 ± 3.3 | 135 | 26.5 ± 3.8 | 19.6 ± 2.8 | 35.5 | 6.6 ± 1.5 | 18.6 ± 4.4 |

Figure 3A:
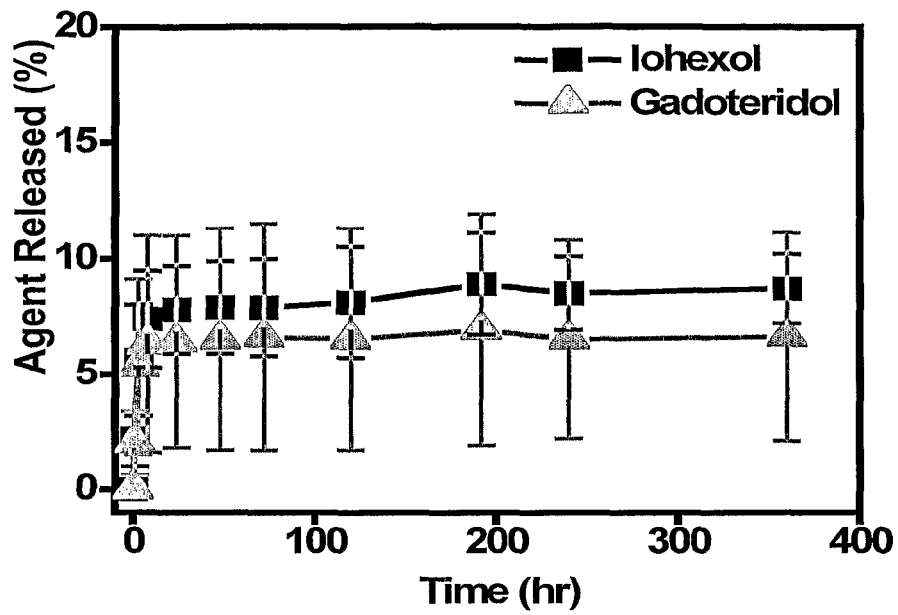
FIG. 3 is an in vitro release profile for Iohexyl and Gadoteridol from DPPC/cholesterol/DSPE-PEG (55/40/5 mol %) liposomes dialyzed under sink conditions (250-fold volume excess) against HBS (a) at 4° C. (n=3) and (b) at 37° C. (n=4)
Figure 3B:
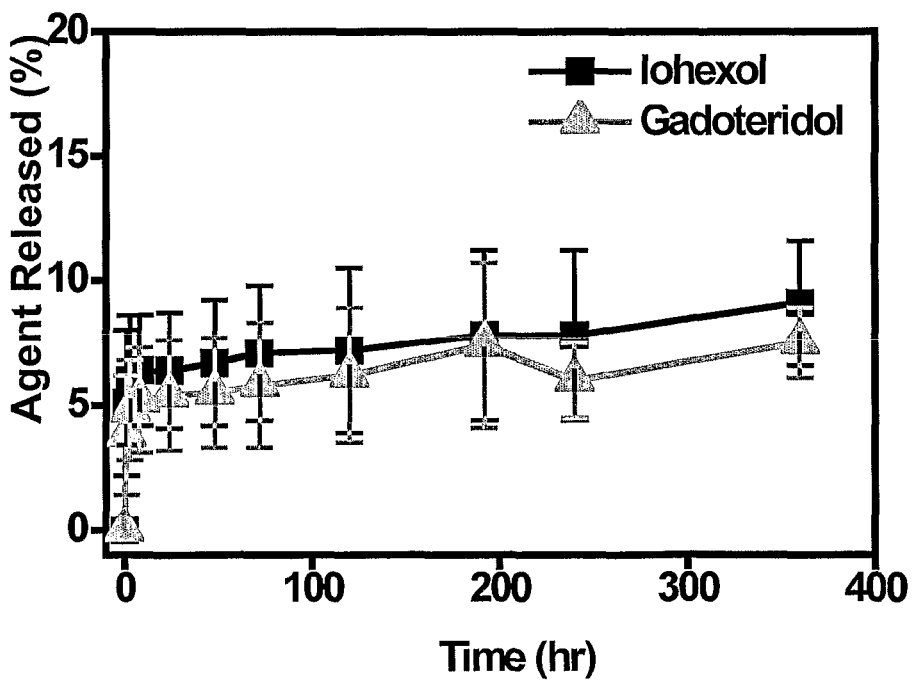
Figure 4:
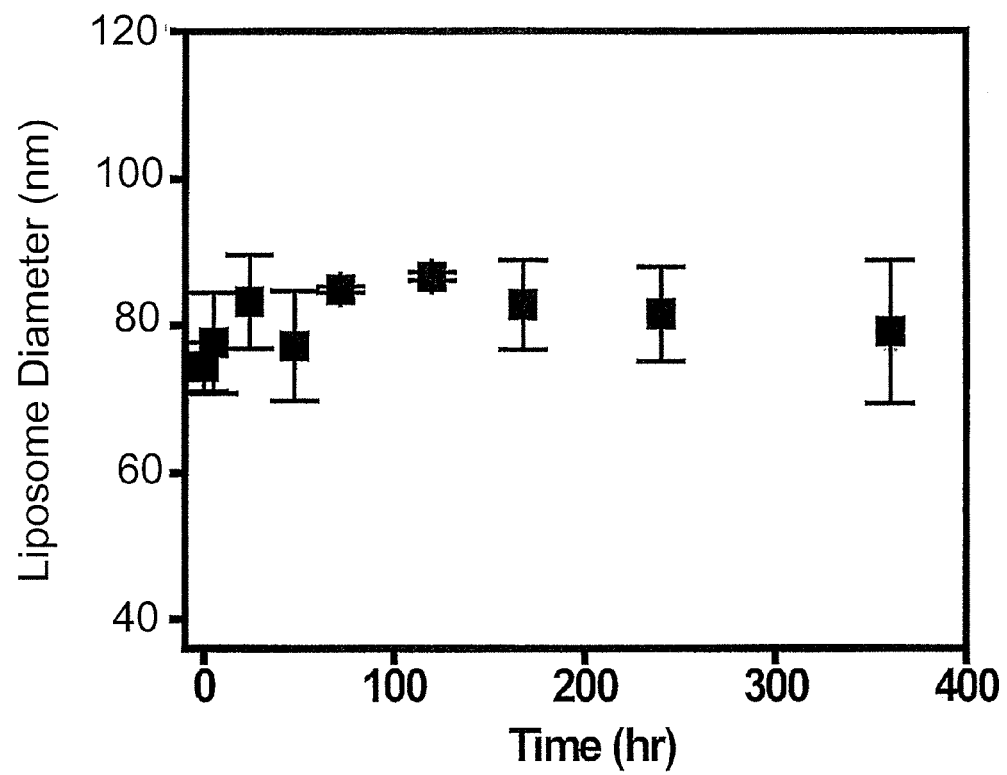
FIG. 4 is a plot of the size of the dual agent-containing liposomes during dialysis under sink conditions (250-fold volume excess) against HBS at 37° C. (n=3)

FIG. 3 includes the in vitro release profile for both agents under sink conditions in physiological buffer at 4° C. (FIG. 3a) and 37° C. (FIG. 3b). As shown, following the 15-day incubation period at 4° C., 8.7±1.5% and 6.6±4.5% of the encapsulated iodine and gadolinium were released, respectively, and at 37° C., 9.1±2.5% and 7.5±1.4% of the encapsulated iodine and gadolinium were released, respectively. The liposomes were also sized periodically during the incubation period in order to assess their stability under sink conditions in HBS at 37° C. As seen in FIG. 4 the liposome size remains constant throughout the incubation period.

In Vitro Imaging

Figure 5A:
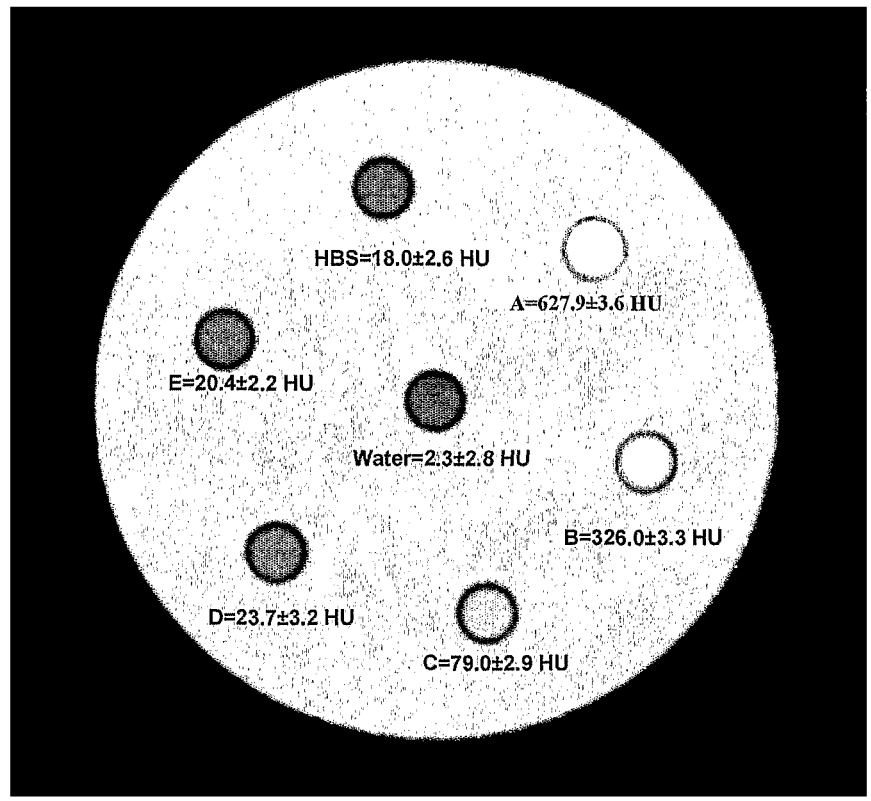
FIG. 5 is an image showing in vitro imaging efficacy of the liposome-based signal modifying agent system (a) in CT (2.5 mm slice thickness, 120 kV, 300 mA and 15.2 cm FOV) and (b) in MRI (450 ms TR, 9 ms TE, 3 mm slice thickness, 19.9 cm FOV and 256×192 image carrier)
Figure 5B:
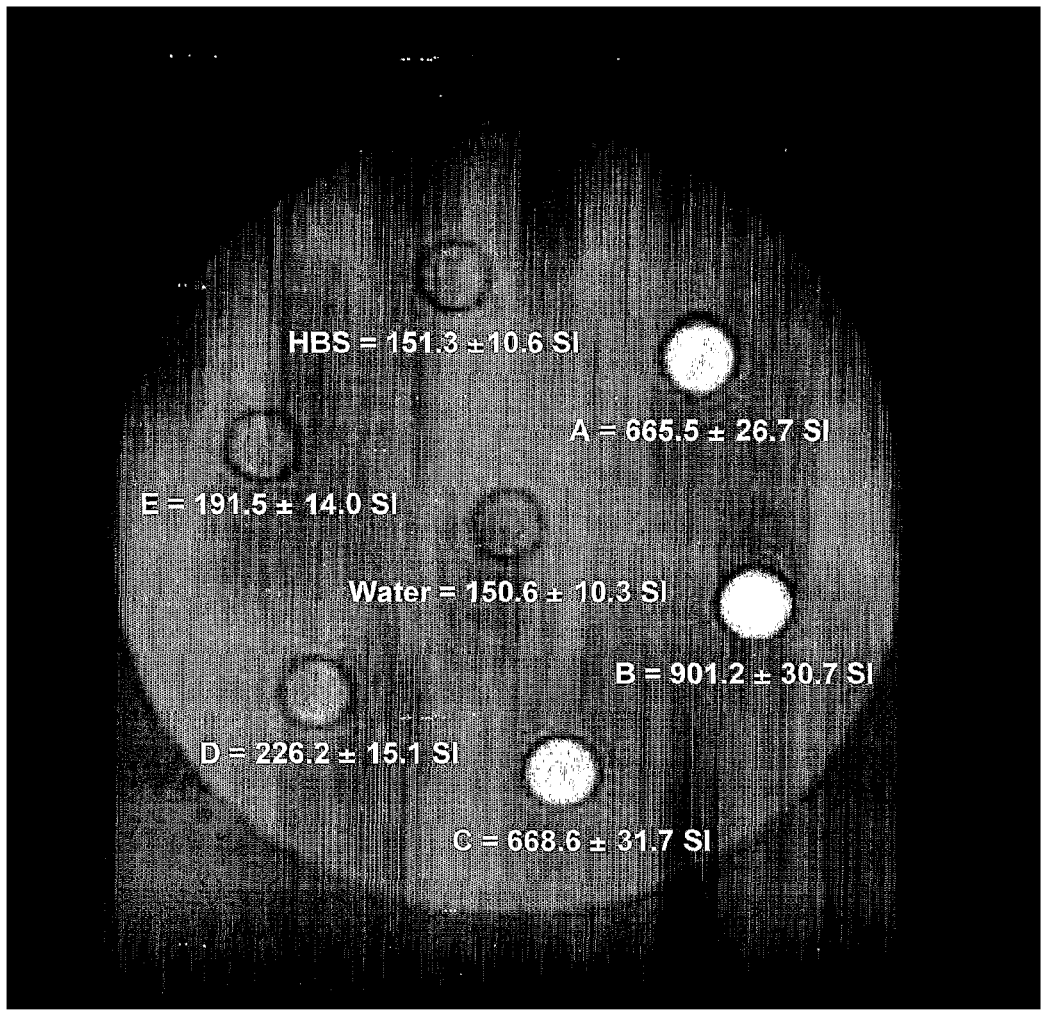

Visual contrast enhancement was observed in CT and MR when the liposome-based signal modifying agent was imaged in vitro at varying concentrations (FIGS. 5a and 5b).

Figure 6A:
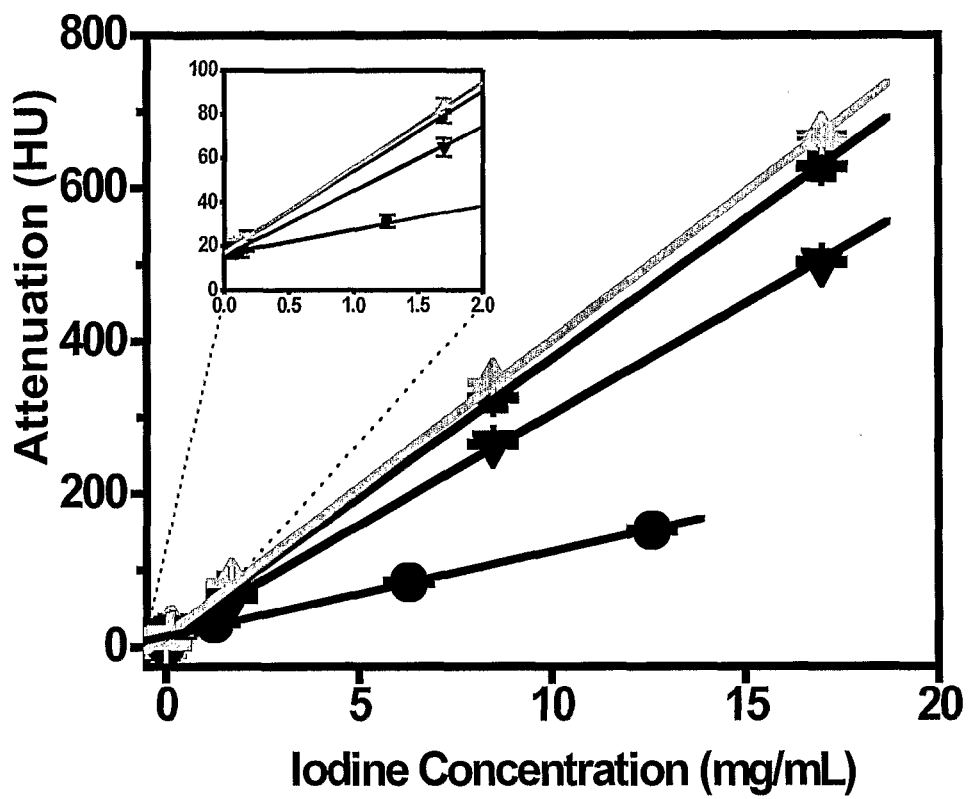

FIG. 6a illustrates the measured CT attenuation of the liposome encapsulated signal modifying agents, the unencapsulated iohexyl, the unencapsulated gadoteridol and the mixture of unencapsulated iohexyl and gadoteridol. Attenuation values varied linearly with concentration for all signal modifying agent solutions. Linear regression analysis revealed an attenuation of 11.1±0.5 HU/(mg of gadolinium) in 1 mL of HBS for the unencapsulated gadoteridol (r=0.99), 29.0±0.4 HU/(mg of iodine) in 1 mL of HBS for the unencapsulated iohexyl (r=0.99), 38.8±0.5 HU/(mg of iodine and 0.2 mg of gadolinium) in 1 mL of HBS for the mixture of unencapsulated iohexyl and gadoteridol (r=0.99), and 36.3±0.5 HU/(mg of iodine and 0.2 mg of gadolinium) in 1 mL of HBS for the liposome formulation (r=0.99). The slightly lower attenuation values observed for the liposome encapsulated iohexyl and gadoteridol compared to free iohexyl and gadoteridol are due to the presence of lipids, which, with respect to water, have lower CT attenuation values (between −60 and −100 HU).

Figure 6B:
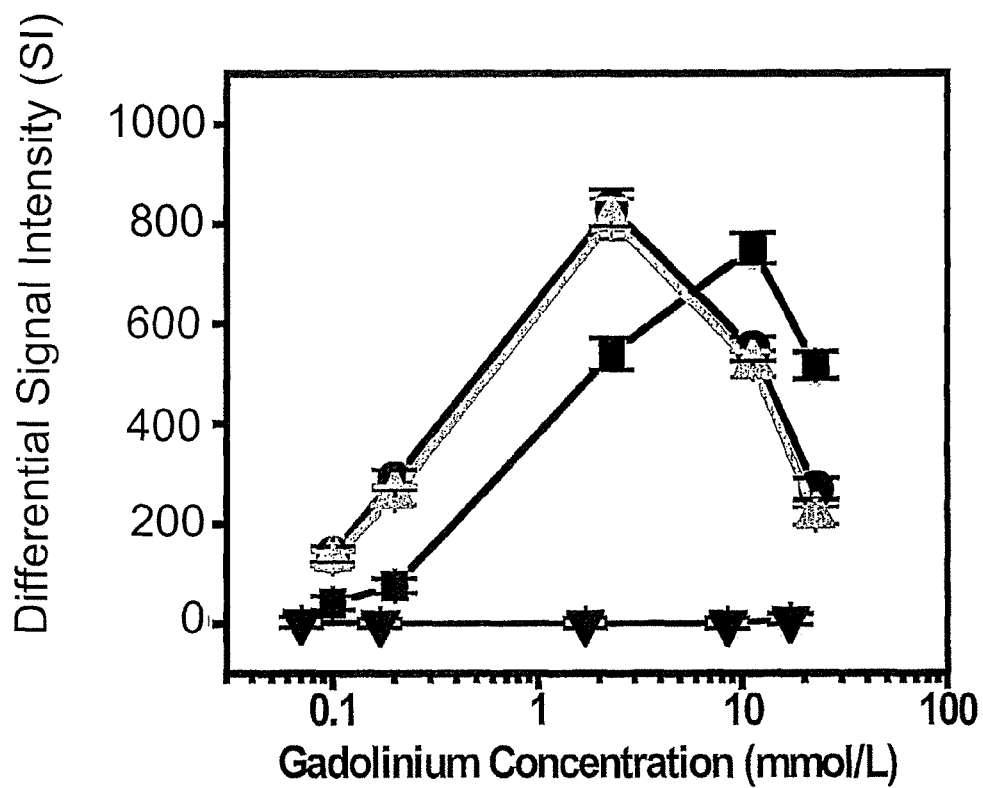

FIG. 6b illustrates the MR relative signal profile as a function of gadolinium concentration. It is known that the linearity between gadolinium concentration and relative signal intensity in MR is lost when critical values of gadolinium concentration are reached (Takeda M, Katayama Y, Tsutsui T, et al. *Tohoku J Exp Med* 1993; 171:119-128; Tweedle M F, Wedeking P, Telser J, et al. *Magn Reson Med* 1991; 22:191-194; discussion 195-196; Morkenborg J, Pedersen M, Jensen F T, et al. *Magn Reson Imaging* 2003; 21:637-643). Furthermore, negative enhancement occurs in MR when the gadolinium concentration reaches high enough levels to cause significant $T_2$ shortening, which in turn causes signal loss (Choyke P L, Frank J A, Girton M E, et al. *Radiology* 1989; 170:713-720; Carvlin M J, Arger P H, Kundel H L, et al. *Radiology* 1989; 170:705-711; May D A, Pennington D J. *Radiology* 2000; 216:232-236; Davis P L, Parker D L, Nelson J A, et al. *Invest Radiol* 1988; 23:381-388). The three plots in FIG. 6b for liposome encapsulated gadoteridol and iohexyl, free gadoteridol and iohexyl and free gadoteridol all exhibit non-linear characteristics. The free iohexyl plot confirms that iodine in the concentration range of 0 to 17 mmol/L shows signal intensity levels comparable to those achieved by water. The average differential signal intensity (SI) in MR for free iohexyl samples was 1.8±7.1 SI relative to water. The unencapsulated gadoteridol samples reached peak differential signal intensities (>600 SI with respect to water) in the gadolinium concentration range of 1 to 9 mmol/L. This is in accordance with previous findings (Morkenborg J, Pedersen M, Jensen F T, et al. *Magn Reson Imaging* 2003; 21:637-643; Choyke P L, Frank J A, Girton M E, et al. *Radiology* 1989; 170:713-720; Carvlin M J, Arger P H, Kundel H L, et al. *Radiology* 1989; 170:705-711; May D A, Pennington D J. *Radiology* 2000; 216:232-236.). A decrease in signal intensity (up to 20%) was observed when free gadoteridol was mixed with iohexyl. This finding is consistent with previous reports on the capability of iodinated signal modifying agents to diminish the signal enhancing effects of gadolinium (Montgomery D D, Morrison W B, Schweitzer M E, et al. *J Magn Reson Imaging* 2002; 15:334-343; Kopka L, Funke M, Fischer U, et al. *AJR Am J Roentgenol* 1994; 163:621; Kopka L, Funke M, Fischer U, et al. *Rofo* 1994; 160:349-352). Encapsulation of gadoteridol and iohexyl in liposome was found to cause a right shift in the differential signal intensity profile (peak signal intensities in MR achieved with gadolinium concentration ranging from 5 to 18 mmol/L). Encapsulation of gadoteridol in the interior of liposomes diminishes MR signal at lower gadolinium concentrations (<5 mmol/L) due to limited bulk water access which decreases $1/T_1$ values (Fossheim S L, Fahlvik A K, Klaveness J, et al. *Magn Reson Imaging* 1999; 17:83-89.). At higher gadolinium concentrations (>5 mmol/L), however, encapsulation of gadoteridol significantly dampens the $T_2$ relaxation effect allowing high signal levels to be maintained over a much broader gadolinium concentration range in MR.

In Vitro Relaxometry

For the relaxometry measurements, $T_1$ (FIG. 7a) and $T_2$ (FIG. 7b) rates were observed to be linear and concentration dependent for both the liposome encapsulated and the unencapsulated signal modifying agents. The $r_1$ and $r_2$ values of unencapsulated gadoteridol were 5.1 and 6.2 $s^{-1}$ $mmol^{-1}$ L, respectively. The $r_1$ and $r_2$ values for gadoteridol in the presence of iohexyl were 6.4 and 7.8 $s^{-1}$ $mmol^{-1}$ L, respectively, and the $r_1$ and $r_2$ values for the liposome encapsulated agents were 1.2 and 1.5 $s^{-1}$ $mmol^{-1}$ L. The $r_1$ and $r_2$ values for iohexyl were found to be 0.0 $s^{-1}$ $mmol^{-1}$ L. Therefore, the encapsulation of the paramagnetic agent gadoteridol in liposomes significantly reduces both the $1/T_1$ and $1/T_2$ relaxivity values, in accordance with FIG. 6b, as well as previously published data (Fossheim S L, Fahlvik A K, Klaveness J, et al. *Magn Reson Imaging* 1999; 17:83-89.).

In Vivo Imaging

FIG. 8 provide an example of how the liposome-based multimodal signal modifying agent can provide structure correspondence for registration and fusion of images acquired from different imaging modalities.

Optical Imaging

Optical contrast enhancement imaging is demonstrated in FIG. 9 wherein a confocal microscopy image of carrier comprising gadoteridol, iohexyl and a fluorophore is shown. Such a carrier would therefore be suitable for MRI, CT and optical imaging or combination thereof.

Examples of multi-modal agents for use in fluorescence optical imaging may include preparation of two types of lipids: (1) phosphatidylethanolamine (PE) conjugated with the fluorescent probe (example: PE-Alexa Fluor 680) and (2) PE conjugated with biotin (i.e. PE-biotin). These lipids can serve as building blocks or components of the lipid bilayer and thus enable the multi-modal agent to support near IR fluorescence optical imaging. Near IR optical fluorescence imaging has the advantage of operating at a wavelength range at which most tissues exhibit low inherent scattering and minimal absorption and it is known to have a higher penetration depth, making it more useful for in vivo imaging applications. Following preparation, liposomes containing the PE-biotin lipid can be incubated with a streptavidin or avidin conjugated fluorescent probe with removal of the excess probe using gel filtration chromatography. It will be appreciated that other approaches to incorporate a fluorophore in the image signal modifier of the invention can be used as would be known to the skilled in the art.

In the case of CT, agents containing elements with high atomic number, such as iodine, are able to increase the differential x-ray attenuation between different soft tissues and organs. Whereas, MR signal modifying agents made up of paramagnetic metals, such as gadolinium, are able to deliver signals by increasing surrounding tissue relaxivity. Furthermore, the differences in intrinsic sensitivity and resolution between the two imaging modalities create a requirement for substantially different concentrations of each reporter moiety in order to achieve adequate signal intensity. For example, in a clinical context, MR is sensitive to gadolinium concentrations between 1-10 µg/mL, while CT requires at least 1 mg/mL of iodine for detection. A multimodal signal modifying composition with efficacy in CT and MR should preferably accommodate this 100-fold differential in sensitivity and minimize any agent-related signal interferences across different imaging modalities.

In a study liposomes were selected as a system for delivery of CT and MR signal modifying agents at appropriate concentrations. Encapsulation of iohexyl in liposomes does not affect the CT attenuation capability of this agent; therefore, as long as a sufficient quantity of iodine is loaded into the interior of the liposomes adequate signal enhancement is expected; although gadolinium relaxation is greatly dependent on the amount of water that the gadolinium atoms can access when encapsulated, the permeability of the liposome membrane can be easily adjusted by varying the lipid composition and cholesterol content (Raffy S, Teissie J. *Biophys J* 1999; 76:2072-2080; Lasic D D. *Trends Biotechnol* 1998; 16:307-321; Drummond D C, Meyer O, Hong K, et al. *Pharmacol Rev* 1999; 51:691-74). In addition, liposomes constitute a highly versatile delivery system. Their size can be easily altered and monodisperse size distributions may be achieved by preparation of the formulation using the high-pressure extrusion method. Also, the surface of liposomes may be modified in order to create vehicles suitable for specific applications. For example, the addition of PEG to the liposome surface has been shown to increase the in vivo circulation lifetime of these vehicles (Allen C, Dos Santos N, Gallagher R, et al. *Biosci Rep* 2002; 22:225-250; Allen T M, Hansen C. *Biochim Biophys Acta* 1991; 1068:133-141). It has also been found that PEGylated liposomes can achieve up to two times higher $r_1$ relaxivity values compared to conventional liposomes. The increase in the $r_1$ relaxivity values for the PEGylated liposomes has been attributed to the presence of PEG-associated water protons in the vicinity of the liposome membrane (Trubetskoy V S, Cannillo J A, Milshtein A, et al. *Magn Reson Imaging* 1995; 13:31-37). Specific moieties may also be conjugated to the liposome surface in order to actively target specific tissues or cells. In this way, with the appropriate surface modifications, liposome-based signal modifying agents may become suitable candidates for use in functional, molecular and optical imaging applications.

Systems for delivery of signal modifying agents for use in blood-pool and lymphatic imaging applications should have minimal agent release in vivo. A stable formulation with slow release profiles for both agents allows for prolonged imaging studies and repeated scans in CT and MR. It is known that extracellular agents with small molecular weights such as iohexyl and gadoteridol have a much faster clearance profile in blood compared to colloidal carriers such as liposomes (Saeed M, Wendland M F, Higgins C B. *J Magn Reson Imaging* 2000; 12:890-898.). Therefore, as the encapsulated agents are released from the liposomes, the signal enhancement will diminish in both CT and MR at a rate that is proportional to that of agent release and clearance. The slow agent release profiles (<9% of each agent released over 15 days, FIG. 3) and stability (liposome size remained unchanged over 15 days, FIG. 4) achieved in vitro for the current liposome formulation provide adequate retention to achieve image enhancement.

Figure 7A:
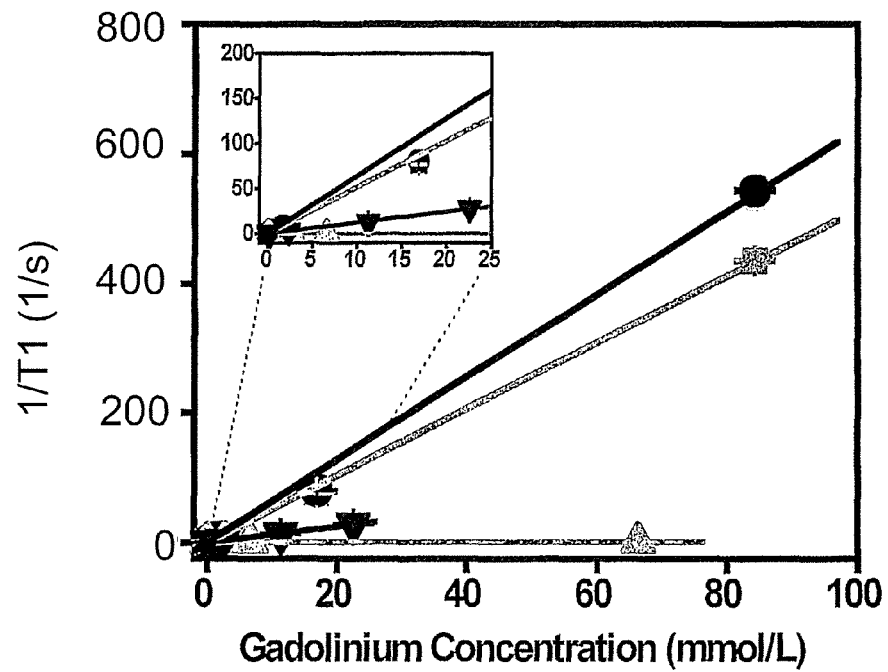
Figure 7B:
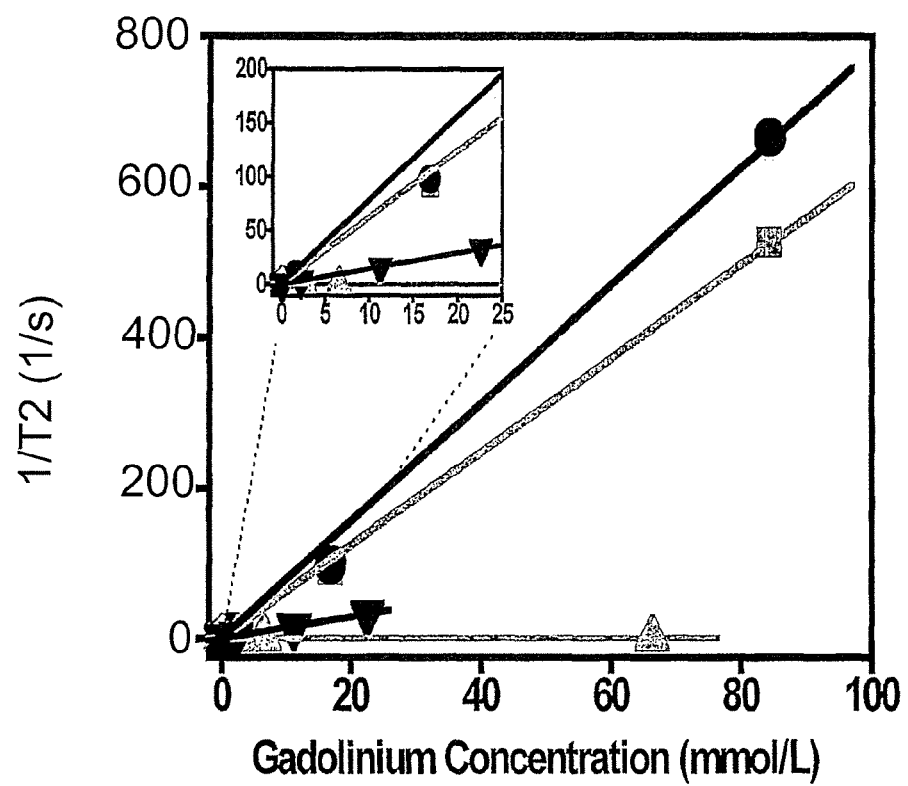

The imaging efficacy in CT and MR of the liposome-based signal modifying agent was assessed in vitro with a purpose-built phantom (FIGS. 5a, 5b, 6a and 6b). The $1/T_1$ and $1/T_2$ relaxivity characteristics of the agent were also investigated (FIGS. 7a and 7b). From the results obtained, it can be concluded that in order to achieve 100 HU of attenuation in CT, ~2.7 mg/mL of the liposome encapsulated iodine is needed, and in order to achieve significant MR enhancement (>600 SI differential signal intensity with respect to water) a minimum of 5 mmol/L (~0.8 mg/mL) of the encapsulated gadolinium is necessary. It will be appreciated that other signal intensity enhancement can be obtained using different concentration of signal modifying agents. The loading characteristics of the current system under investigation (Table 1) allow for significant contrast enhancement in both imaging modalities to be maintained for up to a 10-fold volume dilution following injection.

Example 3

Materials

The following lipids: 1,2-Dipalmitoyl-sn-Glycero-3-Phosphocholine (DPPC, M.W. 734), Cholesterol (CH, M.W. 387) and 1,2-Distearoyl-sn-Glycero-3-Phosphoethanolamine-N-[Poly(ethylene glycol)2000] ($PEG_{2000}DSPE$, M.W. 2774) were purchased from Northern Lipids Inc. (Vancouver, British Columbia, Canada). Omnipaque® was obtained from Nycomed Imaging AS, Oslo, Norway. Omnipaque® (300 mg/mL of iodine) contains iohexyl (M.W. 821.14), an iodinated, water-soluble, non-ionic monomeric contrast medium. ProHance® from Bracco Diagnostics Inc. (Princeton, N.J., USA). ProHance® (78.6 mg/mL of gadolinium) contains gadoteridol (M.W. 558.7), a non-ionic gadolinium complex of 10-(2-hydroxy-propyl)-1,4,7,10-tetraazacyclododecane-1,4,7-triacetic acid.

Liposome Preparation 200 mmol/L of the DPPC, cholesterol and $PEG_{2000}DSPE$ (55:40:5 mole ratio) mixture was dissolved in ethanol at 70° C. and then hydrated with Omnipaque® and Prohance®. The total ethanol content was $10\%_{vol}$. The resulting multilamellar vesicles were sonicated for 1 minute for each mL of liposome solution to yield unilamellar vesicles.

Liposome Characterization

Size and Morphology

The size of liposomes was measured by dynamic light scattering (DLS) at 25° C. using a DynaPro DLS (Protein Solutions, Charlottesville, Va., USA). Transmission electron microscopy (TEM, Hitachi 7000 microscope) was used to assess the liposome morphology. TEM was operated at an acceleration voltage of 75 kV. The liposome sample was first diluted in distilled water and then mixed with phosphotungstic acid (PTA) in a 1:1 volume ratio. The sample solutions were then deposited onto negatively charged and carbon pre-coated copper grids.

In Vivo CT and MR Imaging

The following study was performed under a protocol approved by the University Health Network Animal Care and Use Committee. The female New Zealand white rabbit weighing 2.1 kg was anesthetized with an intramuscular injection of 40 mg/kg of ketamine and 5 mg/mL of xylazine, followed by 2% isoflurane vapor given by inhalation. The signal modifying agent was injected with an automated injector connected to the marginal ear vein catheter at a rate of 1 mL/second. For the MR scan, 10 mL of the signal modifying agent solution (75 mg/kg of iodine and 83 mg/kg of gadolinium encapsulated in liposomes) was injected and flushed with 20 mL of saline solution. MR imaging was performed with a 1.5 Tesla GE Signa TwinSpeed MR scanner (General Electric Medical Systems, Milwaukee, Wis., USA). Scans were produced using a 3D FSGR sequence with a repetition time (TR) of 7.2 ms, an echo time (TE) of 1.6 ms, a slice thickness of 3.4 mm with an overlap of 1.7 mm, a field of view (FOV) of 27.8×27.8 cm and a matrix of 256×224. The signal intensity (SI) was measured in selected tissues using circular regions of interest (ROI).

The CT scan was performed 4 days after the MR scan to allow for complete clearance of the signal modifying agent. For the CT scan 20 mL of the signal modifying agent solution (150 mg/kg of iodine and 166 mg/kg of gadolinium encapsulated in liposomes) was injected and flushed with 20 mL of saline solution. CT imaging was performed using a GE Light-Speed Plus 4-slice helical scanner (General Electric Medical Systems, Milwaukee, Wis., USA) with the following scan parameters: 2.5 mm slice thickness, 120 kV, 200 mA and 49.9×49.9 cm FOV. The mean attenuation in Hounsfield units (HU) in selected regions of interest was measured using ROI.

Both MR and CT scanning sequences were repeated at known time intervals following signal modifying agent injection (3, 5, 7, 10, 15, 20, 25, 30, 45, 60, 75, 90, 105, 120, 135, 150, 165, 180, and 200 minutes).

Results

In Vivo Imaging

Figure 10A:
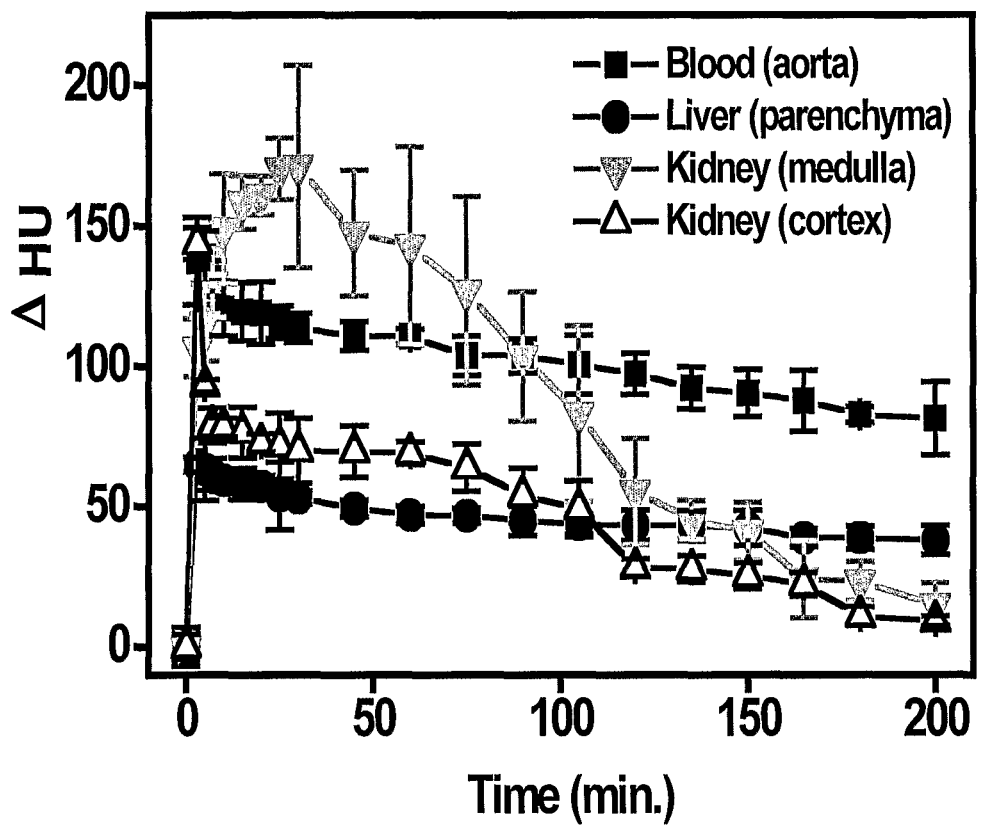
Figure 10B:
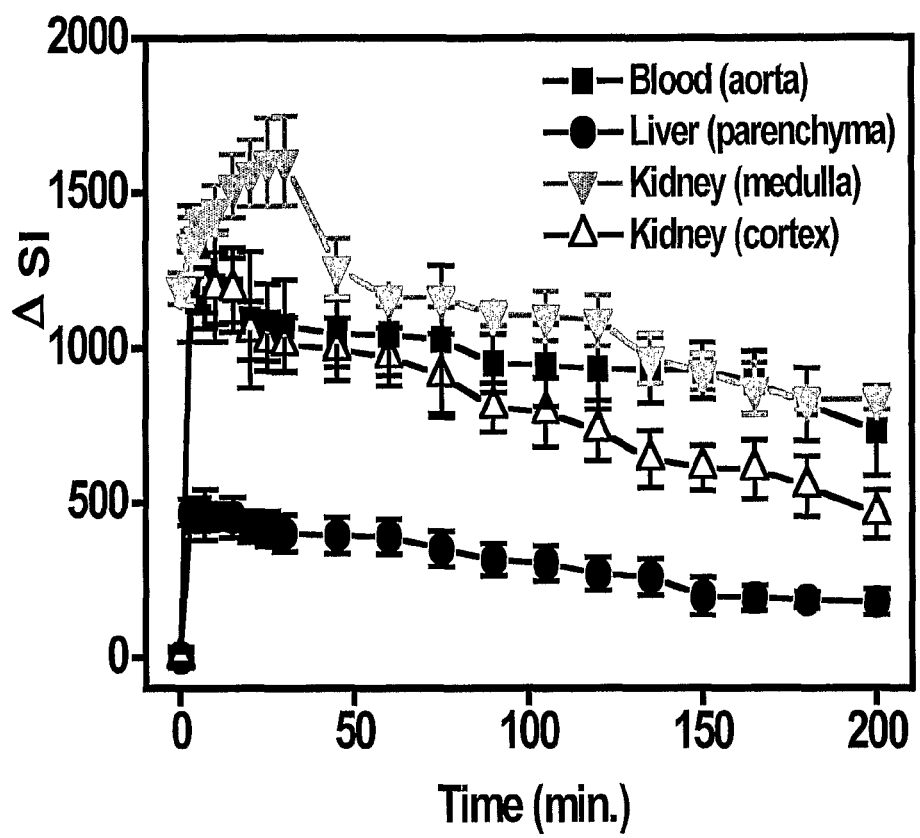

CT and MR image analysis were performed using circular ROI in the aorta, the liver parenchyma, the kidney medulla and cortex before and after injection of signal modifying agent to obtain relative enhancement values. FIG. 10a shows the CT relative attenuation curve vs. time after injection for the tissues of interest. The average differential attenuation was 81.4±13.05 ΔHU in the blood (aorta), 38.0±5.1 ΔHU in the liver parenchyma, 14.8±10.3 ΔHU in the kidney medulla and 9.1±1.7 ΔHU in the kidney cortex 200 minutes following injection. FIG. 10b illustrates the relative signal intensity changes vs. time in MR. At the study endpoint (200 minutes following injection), an enhancement of 731.9±144.2 ΔSI was measured in the aorta, 178.6±41.4 ΔSI in the liver parenchyma, 833.61±33.84 ΔSI in the kidney medulla and 461.7±78.1 ΔSI in the kidney cortex.

Figure 11B:
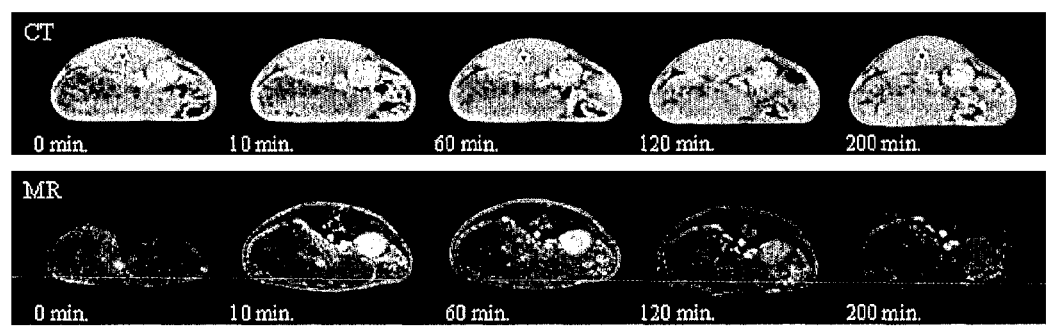

Signal enhancement in the aorta, the liver parenchyma and the kidney cortex reached peak values approximately 10 minutes following the administration of the signal modifying agent. A gradual decrease in signal values occurred over the remaining 190 minutes (FIG. 11a) in both imaging modalities. In the kidney medulla, however, although both the CT and MR differential signal curves peaked 30 minutes following signal modifying agent injection, the CT signal eventually decreased to levels similar to those found in the kidney cortex (consistent with a previously published liposome-based CT agent), while the signal in MR gradually leveled to values similar to those achieved in blood (FIG. 11b).

The impressive in vitro stability and release behavior of this formulation was demonstrated to translate into prolonged in vivo residence times and maintenance of significant signal enhancement both locally (in the liver and kidney) and systemically (in the blood stream) in CT and MR (FIGS. 10 and 11). The substantial signal increase achieved and maintained in the aorta (81.4±13.05 ΔHU in CT and 731.9±144.2 signal intensity ΔSI in MR 200 minutes after injection) suggested that this liposome-based signal modifying agent holds great potential for blood pool imaging, particularly for cardiovascular applications. The enhancement obtained in the liver and the kidney offered insight into the route by which this formulation is cleared in vivo. Based on previously published data, the primary route of clearance for drug-carrying stealth PC liposomes is the liver. This is consistent with the high signals achieved and maintained in the liver parenchyma in both imaging modalities over the course of this study. Without wishing to be bound by any theory, the increase in signal (measured in both CT and MR) in the kidney medulla during the first half hour following administration may be attributed to the initial burst release of the encapsulated agents from the liposomes (refer to FIG. 10). Following release of the encapsulated agents from the liposomes, they are cleared via the renal route due to their low molecular weights. It is worth noting that in CT, 200 minutes post injection, the levels of signal in the kidney medulla and cortex returned to values close to those obtained prior to signal modifying agent injection. While in MR, although the signal in both the medulla and the cortex decreased gradually over time, at the 200 minute time point, the signal measured in the medulla was still significantly higher than that measured in the cortex. A possible explanation for this is the difference in the clearance rates for iohexyl and gadoteridol from the kidneys. The non-linearity in the relationship between MR signal and gadolinium concentration may also have contributed to the difference between the signal levels measured in the kidney medulla for the two imaging modalities.

The parallel and prolonged contrast enhancement achieved in CT and MR makes this signal modifying agent ideal for multimodality image registration. For example, cases of mis-registration due to unpredicted signal variations in different imaging modalities in the regions of interest would be greatly reduced with its use. Its long in vivo residence time will allow for multiple scans to be obtained following a single injection. This in turn will enable the direct correlation of the signals obtained in distinct imaging modalities and allow for correct correspondence between different regions in the image. This multimodal signal modifying agent may also assist in the development of novel image registration techniques, such as biomechanical based registration, which can take advantage of the clear definition of organ boundaries and substructures enhanced in each modality. In addition to improving the performance of image registration techniques, this signal modifying agent may also enhance the ability to identify naturally occurring fiducial points (i.e. vessel bifurcations) used to verify the accuracy of registration techniques.

Example 4

In an additional study, a longitudinal imaging-based assessment of the in vivo stability (FIG. 12) of the signal modifying agent modified liposome was conducted in a rabbit model (2 kg New Zealand White rabbit, 10 mL of the signal modifying agent loaded liposome solution containing 200 mg/kg of iodine and 16 mg/kg of gadolinium). Visual contrast enhancement and measurable signal increases produced by the presence of signal modifying agent carrying liposomes was induced in various organ systems (i.e. heart and blood vessels, liver, spleen, kidney and intestines) in both CT and MR over a 7-day period. Following the extraction of each agent from rabbit plasma, it was determined that 17.7% of the injected iohexyl (95.9 µg/mL of iodine) and 17.3% of the injected gadoteridol (7.9 µg/mL of gadolinium) still circulated in the bloodstream 7 days post-injection. The plasma circulation half-life of the present liposome formulation in rabbits was found to be approximately 45 hours (and approximately 25 hours in Balb-C mice, FIG. 13). A biodistribution study was also performed in Balb-C mice identifying the tissue distribution of liposomes using gadolinium as a surrogate marker (FIG. 14).

Correlations were established between the iodine and gadolinium concentrations found in the rabbit plasma and the signal enhancement obtained in the rabbit aorta in CT and MR, relatively, using circular regions of interest over 6 time points (10 minutes, 24, 48, 72, 120 and 168 hours post-injection). Fairly linear relationships (R2=0.9) were found between the iodine concentration and relative HU increase in CT, and between the gadolinium concentration and relative signal intensity increase in MR (FIG. 15).

Example 5

The signal modifying agents used in CT and MR can be entrapped during liposome preparation; while for optical and radionuclide imaging the specific building blocks (i.e. derivatized lipids) can be incorporated into the lipid bilayer. The commonly employed non-exchangeable, non-metabolizable lipid marker $^3$[H]-cholesterol hexadecyl ether (CHE) can also be incorporated into the liposomes. The signal modifying composition can be administered i.v. via the dorsal tail vein to normal healthy Balb/c mice and animals can be imaged post-administration at specific time points (i.e. 30 mins., 1, 2, 4, 6, 8, 12, 24, 36, 48, 72 hrs.) Also, following each imaging time point, the mice can be sacrificed by cervical dislocation and samples of blood, liver, spleen, kidneys and other tissues excised, weighed and analyzed in order to determine the concentrations of lipid (liquid scintillation counting for $^3$H-CHE), CT agent (HPLC analysis with UV detection for iohexyl), MR agent (ICP-AES for gadoteridol), fluorescence optical agent (HPLC with fluorescence detection) and/or radionuclide ($\gamma$-counter). The ratio of agent or radionuclide to lipid can be calculated for each time point in order to evaluate the retention of agent in the carrier. Also, the results from imaging can be compared to the actual concentration of contrast agent or radionuclide in the blood and tissues in order to determine the sensitivity and linearity of the imaging signal.

Example 6

Active targeting can be evaluated in a well-established mouse tumour xenograft model of human breast cancer that has been used routinely for evaluation of novel radiopharmaceuticals for breast cancer imaging and targeted radiotherapy. The model consists of athymic mice implanted subcutaneously with MDA-MB-468 human breast cancer cells that overexpress epidermal growth factor receptors (EGFR) ($1\times10^6$ EGFR/cell). The EGFR is arguably one of the most well-validated targets on solid tumors ever studied. Interest in targeting the receptor has led to at least two FDA-approved targeted agents for treatment of EGFR-positive malignancies: Iressa™ (Astra-Zeneca), a small molecule tyrosine kinase inhibitor, and Erbitux™ (Imclone), a monoclonal antibody (mAb) directed at the extracellular ligand-binding domain.
Preparation of Actively Targeted Multi-Modal Agents Active targeting can be can be enabled by using derivatized lipids. For example, N-hydroxy succinimydyl ester terminated PEG conjugated PE (PE-PEG-NHS) and biotin terminated PEG conjugated PE (PE-PEG-biotin). The PE-N-PEG-NHS may be used to couple peptides or proteins with a free amino terminus or $\epsilon$-NH$_2$ group to the liposomes (e.g. EGF); while, the PE-N-PEG-biotin may be used to attach the wide range of available biotin functionalized ligands to the liposomes using streptavidin as the coupling agent. EGFR targeted liposomes can be formed from PE-N-PEG-NHS and the mixture of lipids described above (i.e. DPPC, cholesterol and PEG$_{2000}$DSPE). For imaging in CT and MR the agents can be entrapped during liposome preparation; while, for optical and radionuclide imaging the specific building blocks (i.e. derivatized lipids) can be incorporated into the lipid bilayer. Following preparation, the liposomes containing the PE-N-PEG-NHS lipid can be mixed with EGF in PBS for 24 hours and the reaction mixture can then be dialyzed in order to remove the uncoupled EGF. The EGF-conjugation efficiency can be measured using the Micro BCA Protein Assay. The size and stability of the EGF-conjugated-liposomes can be evaluated using DLS. The ability of the EGF-coupled liposomes to interact with their receptors on MDA-MB-468 cells can be evaluated by flow cytometry or by direct or competition radioligand binding assays.
Evaluation of EGFR-Targeted Multi-Modal Agents in Mouse Model of Breast Cancer The liposomes can be administered i.v. via the dorsal tail vein to athymic mice bearing MDA-MB-468 s.c. human breast cancer xenografts (0.25-0.5 cm diameter). The tumour and normal tissue uptake as well as imaging properties of the signal modifying composition can be evaluated. Region-of-interest (ROI) analysis can be performed on the images to evaluate accumulation in the tumour and identifiable organs. Specifically, the kinetics of tumour uptake as well as temporal and spatial distribution of the targeted (and non-targeted liposomes for comparison) can be determined. In addition, following select imaging time points, groups of mice can be sacrificed by cervical dislocation and samples of blood, tumour, liver, spleen, and other tissues excised, weighed and analyzed in order to determine the concentration of lipid and contrast agent (iohexyl, gadoteridol or radionuclide). The specificity of targeting can be evaluated by comparison with imaging and biodistribution studies in mice pre-administered a 500-fold molar express of unconjugated EGF to saturate EGFR on the tumours. A comparison of the tumour and normal tissue uptake of targeted and non-targeted multi-modal contrast agent can also be made, since we expect that some tumour accumulation of the non-targeted agent may occur through the enhanced vascular permeability observed in solid tumours. These multi-modality imaging studies which simultaneously collect two or more signals can reveal important and potentially large differences in the sensitivity of detection of MR, CT and nuclear or fluorescent optical imaging with respect to their capability to detect phentotypic properties of tumours.

The references cited in the present description are all included herein by reference.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A composition for imaging of a biological tissue, the composition comprising:
   a) two or more separate and unlinked signal modifying agents selected from a signal modifying agent specific for computed tomography (CT) and a signal modifying agent specific for positron emission tomography (PET), each of the signal modifying agents being present at a different concentration that is sufficient to acquire in vivo imaging data from an imaging modality for which the signal modifying agent is specific; and
   b) a liposome carrier comprising the two or more signal modifying agents wherein the carrier retains a sufficient amount of the agents for a time sufficient to acquire in vivo imaging data from each of the two or more signal modifying agents using the composition, the liposome comprising at least one lipid, cholesterol (CHOL), and at least one pegylated lipid (PEG lipid), wherein the signal modifying agent specific for PET comprises 64Cu and the signal modifying agent specific for CT comprises iohexol,
wherein the signal modifying agent specific for PET comprises a positron emitting radioisotope and the signal modifying agent specific for CT agent comprises iohexol.

2. The composition of claim 1, wherein the carrier has a retention efficiency of about 10 to about 100% for a time sufficient to acquire imaging data.

3. The composition of claim 1, wherein the carrier has a retention efficiency of about 80 to about 100% for a time sufficient to acquire imaging data.

4. The composition of claim 1, wherein the composition provides signal modification for image data acquisition in the biological tissue for a predetermined amount of time.

5. The composition of claim 1, wherein the predetermined amount of time is between about 1 minute and about 14 days.

6. The composition of claim 1, wherein the predetermined amount of time is between about 5 minutes and about 7 days.

7. The composition of claim 1, wherein the at least one lipid comprises a neutral lipid.

8. The composition of claim 7, wherein the neutral lipid is a phosphatidylcholine (PC).

9. The composition of claim 8, wherein the PC is dipalmitoyl-PC (DPPC).

10. The composition of claim 1, wherein the PEGylated lipid is polyethylene glycol-phosphatidylethanolamine (PEG-PE).

11. The composition of claim 10, wherein the PEG-PE is PEG2000-Distearoyl-PE(PEG2000-DSPE).

12. The composition of claim 1, wherein the lipid, cholesterol and pegylated lipid are in a molar ratio (lipid:CHOL: PEG-lipid) of about 55:40:5.

13. The composition of claim 1, wherein the liposomes have a diameter of between about 30 nm and about 1000 nm.

14. The composition of claim 13, wherein the liposomes have a diameter of between about 30 nm and about 500 nm.

15. The composition of claim 14, wherein the liposomes have a diameter of between about 50 nm and 150 nm.

16. The composition of claim 1, wherein the carrier is targeted to a specific target within a mammal.

17. The composition of claim 16, wherein the targeting is achieved through control of the carrier's physico-chemical properties.

18. The composition of claim 16, wherein the carrier comprises one or more recognition molecules to achieve targeting.

19. The composition of claim 18, wherein the target is a cell population.

20. The composition of claim 18, wherein the one or more recognition molecules are selected from antibodies, receptors/ligands, carbohydrates, proteins and peptide fragments.

21. The composition of claim 1, further comprising a therapeutic agent.

22. The composition of claim 21, wherein the therapeutic agent is selected from anticancer, antimicrobial, antifungal and antiviral agents.

23. The composition of claim 1, wherein the liposome releases <9% of each of the signal modifying agents over 15 days when dialyzed under sink conditions against HBS at 4° C. or 37° C.

24. A method for imaging one or more regions of interest in a mammal, the method comprising:
a) administering to the mammal the composition of claim 1;
b) waiting for a time sufficient for the composition to reach the region of interest; and
c) obtaining two or more images of the one or more regions of interest.

25. The method of claim 24, wherein the step of waiting further comprises waiting for a time sufficient for the composition to substantially clear from a predetermined region.

26. The method of claim 24, wherein the regions of interest comprise an abnormality and wherein the abnormality is detected in the images.

27. The method of claim 26, wherein the abnormality is a tumor.

28. A method for registering images obtained from two or more imaging modalities the method comprising:
a) administering to a mammal a composition of claim 1, each agent being specific for at least one of the two or more imaging modalities;
b) obtaining an image of one or more regions of interest in the mammal using each of the two or more imaging modalities; and
c) comparing the images obtained in b) to derive complementary information from the one or more regions of interest.

29. The method of claim 28, wherein the complementary information is selected from anatomical information, molecular information, functional information, physiological information and combinations thereof.

30. The method of claim 24, further comprising the step of estimating a pharmacokinetic profile of the composition.

31. The method of claim 30, further comprising the step of designing an administration regimen based on the pharmacokinetic profile.

32. The method of claim 31, wherein the administration regimen is applied to a patient in need thereof.

33. The method of claim 32, wherein progress of the administration regimen is followed over time by obtaining one or more images after the regimen is started.

34. The method of claim 31, wherein the composition further comprises a therapeutic agent.

35. The method of claim 31, wherein the administration regimen is a regimen for treating cancer.

36. The method of claim 35, wherein the regimen is selected from surgery, radiotherapy, chemotherapy, cell therapy, gene therapy and hyperthermia.

37. The composition of claim 1, wherein the signal modifying agent specific for PET comprises $^{64}$Cu.

* * * * *